(12) United States Patent
Garland et al.

(10) Patent No.: US 7,691,622 B2
(45) Date of Patent: Apr. 6, 2010

(54) METHOD AND APPARATUS FOR TRANSFERRING HEAT TO OR FROM AN ORGAN OR TISSUE CONTAINER

(75) Inventors: Jeffrey C. Garland, Littleton, CO (US); Douglas Schein, Arlington Heights, IL (US); David Walter Wright, Littleton, CO (US)

(73) Assignee: Lifeline Scientific, Inc., Itasca, IL (US)

( * ) Notice: Subject to any disclaimer, the term of this patent is extended or adjusted under 35 U.S.C. 154(b) by 1138 days.

(21) Appl. No.: 10/815,853

(22) Filed: Apr. 2, 2004

(65) Prior Publication Data

US 2004/0224299 A1 Nov. 11, 2004

Related U.S. Application Data

(60) Provisional application No. 60/459,986, filed on Apr. 4, 2003.

(51) Int. Cl.
*A01N 1/02* (2006.01)
*F25D 3/08* (2006.01)

(52) U.S. Cl. .................. 435/284.1; 435/1.2; 435/303.1; 435/307.1; 435/809; 62/457.1

(58) Field of Classification Search .............. 435/284.1, 435/307.1, 1.4, 303.1, 809; 62/237, 457.9, 62/3.62, 371, 872, 457.1, 457.2
See application file for complete search history.

(56) References Cited

U.S. PATENT DOCUMENTS

| | | | |
|---|---|---|---|
| 1,369,367 A * | 2/1921 | Thomson | 220/592.14 |
| 1,682,344 A | 8/1928 | Lesieur | |
| 1,916,658 A | 7/1933 | Davidson | |
| 3,406,531 A | 10/1968 | Swenson et al. | |
| 3,545,221 A | 12/1970 | Swenson et al. | |
| 3,607,646 A | 9/1971 | de Roissart | |
| 3,632,473 A | 1/1972 | Belzar | |
| 3,639,084 A | 2/1972 | Goldhaber | |
| 3,654,085 A | 4/1972 | Norr et al. | |
| 3,660,241 A | 5/1972 | Michielsen | |
| 3,712,583 A | 1/1973 | Martindale et al. | |
| 3,713,302 A * | 1/1973 | Reviel | 62/3.62 |
| 3,738,914 A | 6/1973 | Thorne et al. | |

(Continued)

FOREIGN PATENT DOCUMENTS

EP 376763 A2 * 7/1990

(Continued)

OTHER PUBLICATIONS

U.S. Appl. No. 60/459,981, filed Apr. 4, 2003, David W. Wright et al.

(Continued)

*Primary Examiner*—William H Beisner
(74) *Attorney, Agent, or Firm*—Oliff & Berridge, PLC.

(57) ABSTRACT

An organ perfusion apparatus and method monitor, sustain and/or restore viability of organs and preserve organs for storage and/or transport. Other apparatus include an organ transporter, an organ cassette and an organ diagnostic device. The apparatus and methods include the cassette and transporter with heat transfer surfaces arranged to transfer heat between a cooling source in said transporter and the heat transfer surfaces of the cassette.

62 Claims, 13 Drawing Sheets

U.S. PATENT DOCUMENTS

| | | |
|---|---|---|
| 3,753,865 A | 8/1973 | Belzer et al. |
| 3,772,153 A | 11/1973 | de Roissart |
| 3,777,507 A | 12/1973 | Burton et al. |
| 3,810,367 A | 5/1974 | Peterson |
| 3,843,455 A | 10/1974 | Bier |
| 3,845,974 A | 11/1974 | Pelloux-Gervais |
| 3,877,843 A | 4/1975 | Fischel |
| 3,881,990 A | 5/1975 | Burton et al. |
| 3,892,628 A | 7/1975 | Thorne et al. |
| 3,914,954 A | 10/1975 | Doerig |
| 3,935,065 A | 1/1976 | Doerig |
| 3,962,439 A | 6/1976 | Yokoyama et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,242,883 A | 1/1981 | Toledo-Pereyra |
| 4,243,883 A | 1/1981 | Schwarzmann |
| 4,378,797 A | 4/1983 | Osterholm |
| 4,393,863 A | 7/1983 | Osterholm |
| 4,445,500 A | 5/1984 | Osterholm |
| 4,451,251 A | 5/1984 | Osterholm |
| 4,462,215 A | 7/1984 | Kuraoka et al. |
| 4,471,629 A | 9/1984 | Toledo-Pereyra |
| 4,473,637 A | 9/1984 | Guibert |
| 4,474,016 A | 10/1984 | Winchell |
| 4,494,385 A | 1/1985 | Kuraoka et al. |
| 4,502,295 A | 3/1985 | Toledo-Pereyra |
| 4,530,816 A * | 7/1985 | Douglas-Hamilton .......... 422/1 |
| 4,559,298 A | 12/1985 | Fahy |
| 4,596,250 A | 6/1986 | Beisang, III et al. |
| 4,618,586 A | 10/1986 | Walker |
| 4,629,686 A | 12/1986 | Gruenberg |
| 4,657,532 A | 4/1987 | Osterholm |
| 4,666,425 A | 5/1987 | Fleming |
| 4,704,029 A | 11/1987 | Van Heuvelen |
| 4,717,548 A | 1/1988 | Lee |
| 4,723,974 A | 2/1988 | Ammerman |
| 4,745,759 A | 5/1988 | Bauer et al. |
| 4,766,740 A | 8/1988 | Bradley et al. |
| 4,801,299 A | 1/1989 | Brendel et al. |
| 4,837,390 A | 6/1989 | Reneau |
| 4,879,283 A | 11/1989 | Belzer et al. |
| 4,951,482 A | 8/1990 | Gilbert |
| 4,958,506 A | 9/1990 | Guilhem et al. |
| 5,003,787 A | 4/1991 | Zlobinsky |
| 5,013,303 A | 5/1991 | Tamari et al. |
| 5,028,588 A | 7/1991 | Hoffman et al. |
| 5,036,097 A | 7/1991 | Floyd et al. |
| 5,047,395 A | 9/1991 | Wu |
| 5,051,352 A | 9/1991 | Martindale et al. |
| 5,066,578 A | 11/1991 | Wikman-Coffelt |
| 5,085,630 A | 2/1992 | Osterholm et al. |
| 5,110,721 A | 5/1992 | Anaise et al. |
| 5,130,230 A | 7/1992 | Segall et al. |
| 5,141,847 A | 8/1992 | Sugimachi et al. |
| 5,145,771 A | 9/1992 | Lemasters et al. |
| 5,149,321 A | 9/1992 | Klatz et al. |
| 5,157,930 A | 10/1992 | McGhee et al. |
| 5,200,176 A | 4/1993 | Wong et al. |
| 5,216,032 A | 6/1993 | Manning |
| 5,217,860 A | 6/1993 | Fahy et al. |
| 5,234,405 A | 8/1993 | Klatz et al. |
| 5,285,657 A | 2/1994 | Bacchi et al. |
| 5,326,706 A | 7/1994 | Yland et al. |
| 5,328,821 A | 7/1994 | Fisher et al. |
| 5,338,662 A | 8/1994 | Sadri |
| 5,356,771 A | 10/1994 | O'Dell |
| 5,362,622 A | 11/1994 | O'Dell et al. |
| 5,383,854 A | 1/1995 | Safar et al. |
| 5,385,821 A | 1/1995 | O'Dell et al. |
| 5,395,314 A | 3/1995 | Klatz et al. |
| 5,434,045 A | 7/1995 | Jost |
| 5,437,633 A | 8/1995 | Manning |
| 5,472,876 A | 12/1995 | Fahy |
| 5,476,763 A | 12/1995 | Bacchi et al. |
| 5,494,822 A | 2/1996 | Sadri |
| 5,584,804 A | 12/1996 | Klatz et al. |
| 5,586,438 A | 12/1996 | Fahy |
| 5,599,659 A | 2/1997 | Brasile et al. |
| 5,622,429 A | 4/1997 | Heinze |
| 5,643,712 A | 7/1997 | Brasile |
| 5,681,740 A | 10/1997 | Messier et al. |
| 5,699,793 A | 12/1997 | Brasile |
| 5,702,881 A | 12/1997 | Brasile et al. |
| 5,709,654 A | 1/1998 | Klatz et al. |
| 5,712,084 A | 1/1998 | Osgood |
| 5,716,378 A | 2/1998 | Minten |
| 5,723,282 A | 3/1998 | Fahy et al. |
| 5,730,720 A | 3/1998 | Sites et al. |
| 5,752,929 A | 5/1998 | Klatz et al. |
| 5,821,045 A | 10/1998 | Fahy et al. |
| 5,823,986 A | 10/1998 | Peterson |
| 5,827,222 A | 10/1998 | Klatz et al. |
| 5,843,024 A | 12/1998 | Brasile |
| 5,856,081 A | 1/1999 | Fahy |
| 5,879,329 A | 3/1999 | Ginsburg |
| 5,928,182 A | 7/1999 | Kraus et al. |
| 5,965,433 A | 10/1999 | Gardetto et al. |
| 6,024,698 A | 2/2000 | Brasile |
| 6,046,046 A | 4/2000 | Hassanein |
| 6,100,082 A | 8/2000 | Hassanein |
| 6,673,594 B1 | 1/2004 | Owen et al. |
| 6,677,150 B2 | 1/2004 | Alford et al. |

FOREIGN PATENT DOCUMENTS

| | | |
|---|---|---|
| WO | WO 86/00812 | 12/1986 |
| WO | WO 91/09520 | 7/1991 |
| WO | WO 94/06292 | 3/1994 |
| WO | WO 96/12191 | 4/1996 |
| WO | WO 96/29865 | 10/1996 |
| WO | WO 96/30111 | 10/1996 |
| WO | WO 96/31779 | 10/1996 |
| WO | WO 96/32074 | 10/1996 |
| WO | WO 96/32157 | 10/1996 |
| WO | WO 97/22003 | 6/1997 |
| WO | WO 97/28449 | 8/1997 |
| WO | WO 88/05261 | 7/1998 |
| WO | WO 00/18226 | 4/2000 |

OTHER PUBLICATIONS

U.S. Appl. No. 60/460,875, filed Apr. 8, 2003, David W. Wright et al.
"Randomized Clinical Study of Thiopental Loading in Comatose Survivors of Cardiac Arrest", *The New England Journal of Medicine*, vol. 314, No. 7, pp. 397-403, Feb. 1996.
"Free Radicals and Myocardial Ischemia and Reperfusion Injury", Paul J. Simpson et al., *J Lab Cin Med.*, pp. 13-30, Jul. 1987.
"Development of an Isolated Perfused Dog Kidney With Improved Function", William H. Waugh et al., *American Journal of Physiology*, vol. 217, No. 1, Jul. 1969.
"Variations in Vascular Resistance of Isolated Rat Hearts During Normothermic and Hypotermic Experiments", C.G. Adem et al., *J. Biomed. Engng.*, vol. 3(2), pp. 128-133, 1981.
"Effect of Pharmacologic Agents on the Function of the Hypothermically Preserved Dog Kidney During Normothermic Reperfusion", Rutger J. Ploeg et al., *Surgery*, vol. 103, No. 6, pp. 676-682, Jun. 1988.
"The Beneficial Effect of Intermediate Normothermic Perfusion During Cold Storage of Ischemically Injured Kidneys", Jos G. Maessen et al., *Transplantation*, vol. 47, No. 3, pp. 409-414, Mar. 1989.
"The Asystolic, or Non-Heartbeating, Donor", Gauke Kootstra, *Transplantation*, vol. 63, No. 7, pp. 917-921, 1997.

"Normothermic Renal Artery Perfusion: a Comparison of Perfusates", John D. Hughes et al., *Annals of Vascular Surgery*, vol. 10, pp. 123-130, 1996.

"Is Normothermic Preservation an Alternative to Hypothermic Preservation?", R. N. Dunn et al., *Organ Preservation Basic and Applied Aspects*, Chapter 38, pp. 273-277, 1982.

"Studies of Controlled Reperfusion After Ischemia", Pierre L. Julia, MD et al., *The Journal of Thoracic and Cardiovascular Surgery*, vol. 101, No. 2, pp. 303-313, Feb. 1991.

"Urinary π-Class Glutathione Transferase as an Indicator of Tubular Damage in the Human Kidney", Dr. Anders Sundberg et al., *Nephron*, vol. 67, pp. 308-316, 1994.

"Effect of Ischemia and 24 Hour Reperfusion on ATP Synthesis in the Rat Kidney", C.E. Irazu et al., *Journal of Experimental Pathology*, vol. 4, No. 1, pp. 29-36, 1989.

"Intermediate Normothermic Hemoperfusion of Rat Kidneys: Functional Aspects and a Study Into The Effect of Free Radical Scavengers", A.O. Gaber, *Transplantation Proceedings*, vol. XX, No. 5, pp. 896-898, Oct. 1998.

"Improvement of Postischemic Kidney Function by Reperfusion With a Specifically Developed Solution (BT01)", Pierre Julia, MD et al., *Annals of Vascular Surgery*, vol. 9, pp. S-81-s-88, 1995.

"Ischemia With Intermittent Reperfusion Reduces Functional and Morphologic Damage Following renal Ischemia in the Rat", Richard S. Frank, MD et al., *Annals of Vascular Surgery*, vol. 7, No. 2, pp. 150-155, 1993.

"Graft Conditioning of Liver in Non-Heart-Beating Donors by an Artificial Heart and Lung Machine in Situ", T. Endoh et al., *Transplantation Proceedings*, vol. 28, No. 1, pp. 110-115, Feb. 1996.

"Machine Perfusion of Isolated Kidney at 37°C. Using Pyridoxalated Hemoglobin-Polyoxyethlene (PHP) Solution, UW Solution and its Combination", T. Horiuchi et al., *Biomaterials, Art. Cells & Immob. Biotech*, vol. 20, Nos. 2-4,, pp. 549-555, 1992.

"Analysis of the Optimal Perfusion Pressure and Flow Rate of the Renal Vascular Resistance and Oxygen Consumption in the Hypothermic Perfused Kidney", R. Grundmann, M. D. et al., *Surgery*, vol. 77, No. 3, pp. 451-461, Mar. 1975.

"An Experimental Model for Assessment of Renal Recovery From Warm Ischemia", Paula Jablonski et al., *Transplantation*, vol. 35, No. 3, pp. 198-204, Mar. 1983.

B.G. Rijkmans et al., "Six-Day Canine Kidney Preservation, Hypothermic Perfusion Combined with Isolated Blood Perfusion, " Feb. 1984, pp. 130-134.

"Intermediate Normothermic Perfusion During Cold Storage of Ischemically Injured Kidney," J.G. Maessen et al., Transplantation Proceedings, vol. 21, No. 1, Feb. 1989, pp. 1252-1253.

\* cited by examiner

METHOD AND APPARATUS FOR TRANSFERRING HEAT TO OR FROM AN ORGAN OR TISSUE CONTAINER

This application is a non-provisional application claiming priority to provisional U.S. Patent Application No. 60/459,986 filed Apr. 4, 2003.

BACKGROUND OF THE INVENTION

The invention relates to apparatus and methods for perfusing one or more organs, tissues or the like (hereinafter generally referred to as organs) to monitor, sustain and/or restore viability of the organs. This invention further relates to allowing effective heat transfer to or from the contents of a portable cassette.

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654, 5,752,929 and 5,827,222 to Klatz et al., which are hereby incorporated by reference. Hypothermic temperatures provide a decrease in organ metabolism, lower energy requirements, delay depletion of high energy phosphate reserves and accumulation of lactic acid and retard morphological and functional deterioration associated with disruption of blood supply.

Ideally organs would be procured in a manner that limits their warm ischemia time to essentially zero. Unfortunately, in reality, many organs, especially from non-beating heart donors, are procured after extended warm ischemia time periods (i.e., 45 minutes or more). The machine perfusion of these organs at low temperature has demonstrated significant improvement (Transpl Int 1996 Daemen). Further, prior art teaches that the low temperature machine perfusion of organs is preferred at low pressures (Transpl. Int 1996 Yland) with roller or diaphragm pumps delivering the perfusate at a controlled pressure. Numerous control circuits and pumping configurations have been utilized to achieve this objective and to machine perfuse organs in general. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thorne et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al.

WO 88/05261 to Owen discloses an organ perfusion system including an organ chamber that is supplied with an emulsion fluid or physiological electrolyte that is transported through a perfusion system. The chamber contains a synthetic sac to hold the organ. Perfusate enters the organ through a catheter inserted into an artery. The perfusate is provided by two independent fluid sources, each of which includes two reservoirs.

SUMMARY OF THE INVENTION

The present invention focuses on avoiding damage to an organ during perfusion while monitoring, sustaining and/or restoring the viability of the organ and preserving the organ for storage and/or transport. The invention is directed to apparatus and methods for perfusing an organ to monitor, sustain and/or restore the viability of the organ and/or for transporting and/or storing the organ.

In perfusion, gross organ perfusion pressure may be provided by a pneumatically pressurized medical fluid reservoir controlled in response to a sensor disposed in an end of tubing placed in the organ, which may be used in combination with a stepping motor/cam valve or pinch valve which provides for perfusion pressure fine tuning, prevents over pressurization and/or provides emergency flow cut-off. Alternatively, the organ may be perfused directly from a pump, such as a roller pump or a peristaltic pump, with proper pump control and/or sufficiently fail-safe controllers to prevent over pressurization of the organ, especially as a result of a system malfunction. Substantially eliminating over pressurization prevents and/or reduces damage to the vascular endothelial lining and to the organ tissue in general.

Apparatus of the invention may be used for various organs, such as the kidneys, and may be adapted to more complex organs, such as the liver, having multiple vasculature structures, for example, the hepatic and portal vasculatures of the liver.

An organ diagnostic apparatus may also be provided to produce diagnostic data such as an organ viability index. The organ diagnostic apparatus includes features of an organ perfusion apparatus, such as sensors and temperature controllers, as well as cassette interface features, and provides analysis of input and output fluids in a perfusion system. Typically, the organ diagnostic apparatus is a simplified perfusion apparatus providing diagnostic data in a single pass, in-line perfusion.

Embodiments of the invention also provide an organ cassette which allows an organ to be easily and safely moved between apparatus for perfusing, storing, analyzing and/or transporting the organ. The organ cassette may be configured to provide uninterrupted sterile conditions and efficient heat transfer during transport, recovery, analysis and storage, including transition between the transporter, perfusion apparatus and organ diagnostic apparatus, and/or other apparatus.

Embodiments of this invention also provide an organ transporter which allows for transportation of an organ, particularly over long distances. The organ transporter may include features of an organ perfusion apparatus, such as sensors and temperature controllers, as well as cassette interface features.

Embodiments of this invention provide a cooling source in the transporter.

Embodiments of this invention provide the cassette and a compartment of the transporter with one or more heat transfer surfaces which contact and allow effective heat transfer to or from the contents of the cassette.

Embodiments of this invention provide the cassette and the compartment of the transporter with substantially complementary mating configurations.

Embodiments of this invention provide for planar and non-planar heat transferring surfaces.

These and other features and advantages of this invention are described in, or are apparent from, the following detailed description of various exemplary embodiments of systems and methods according to this invention.

BRIEF DESCRIPTION OF THE DRAWINGS

The above and other aspects and advantages of the invention will become apparent from the following detailed description of embodiments when taken in conjunction with the accompanying drawings, in which.

DETAILED DESCRIPTION OF PREFERRED EMBODIMENTS

Figure 1:
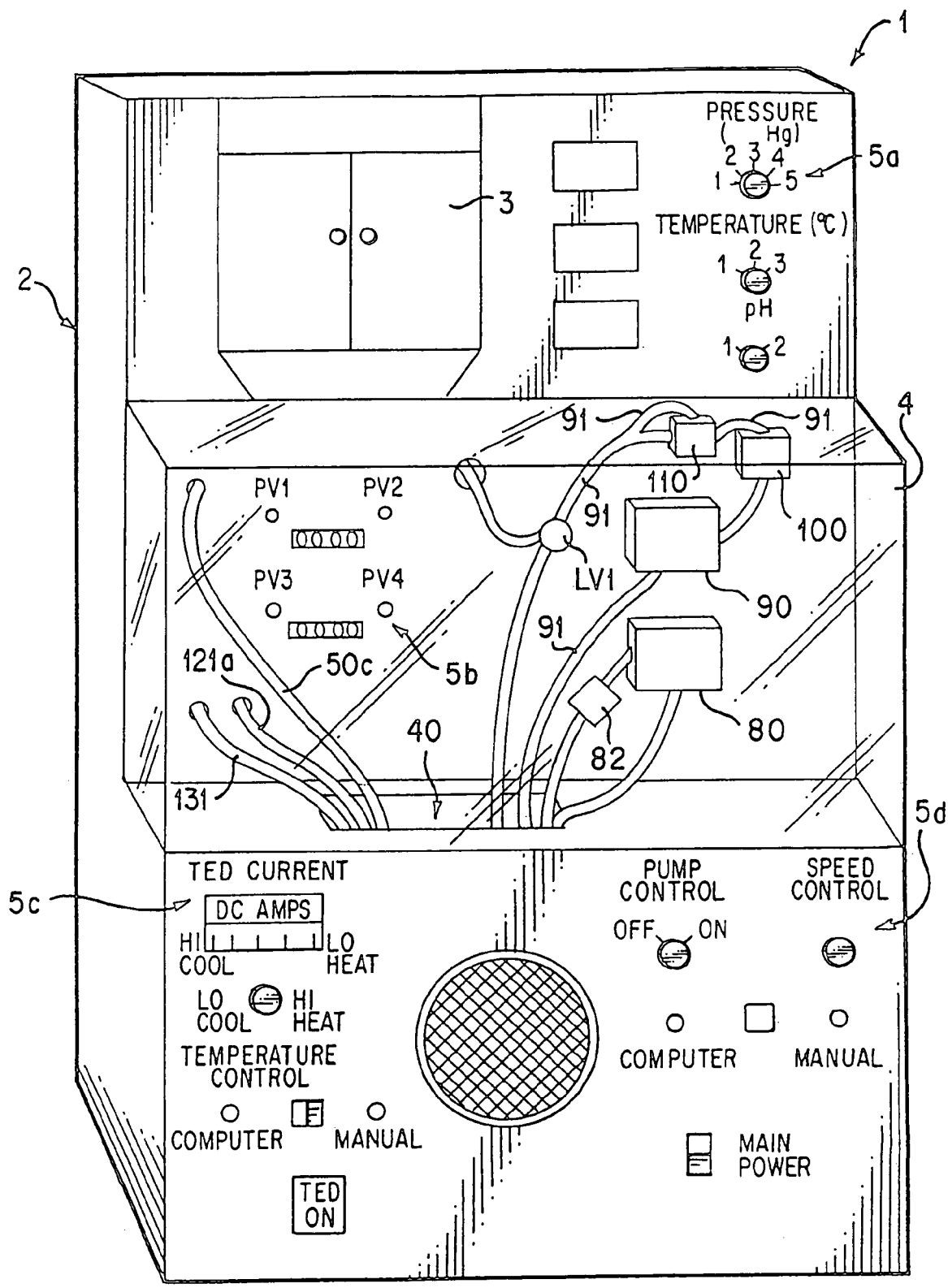
FIG. 1 is an organ perfusion apparatus according to the invention.

For a general understanding of the features of the invention, reference is made to the drawings. In the drawings, like reference numerals have been used throughout to designate like elements.

The invention is described herein largely in the context of apparatus and methods involved in transport, storage, perfusion and diagnosis of tissues and organs. However, the inventive apparatus and methods have many other applications, and thus the various inventive structures, devices, apparatus and methods described herein should not be construed to be limited to, particular contexts of use. Various features of the disclosed invention are particularly suitable for use in the context of, and in conjunction and/or connection with the features of the apparatus and methods disclosed in U.S. patent application Ser. No. 09/645,525, the entire disclosure of which is hereby incorporated by reference herein.

Figure 2:
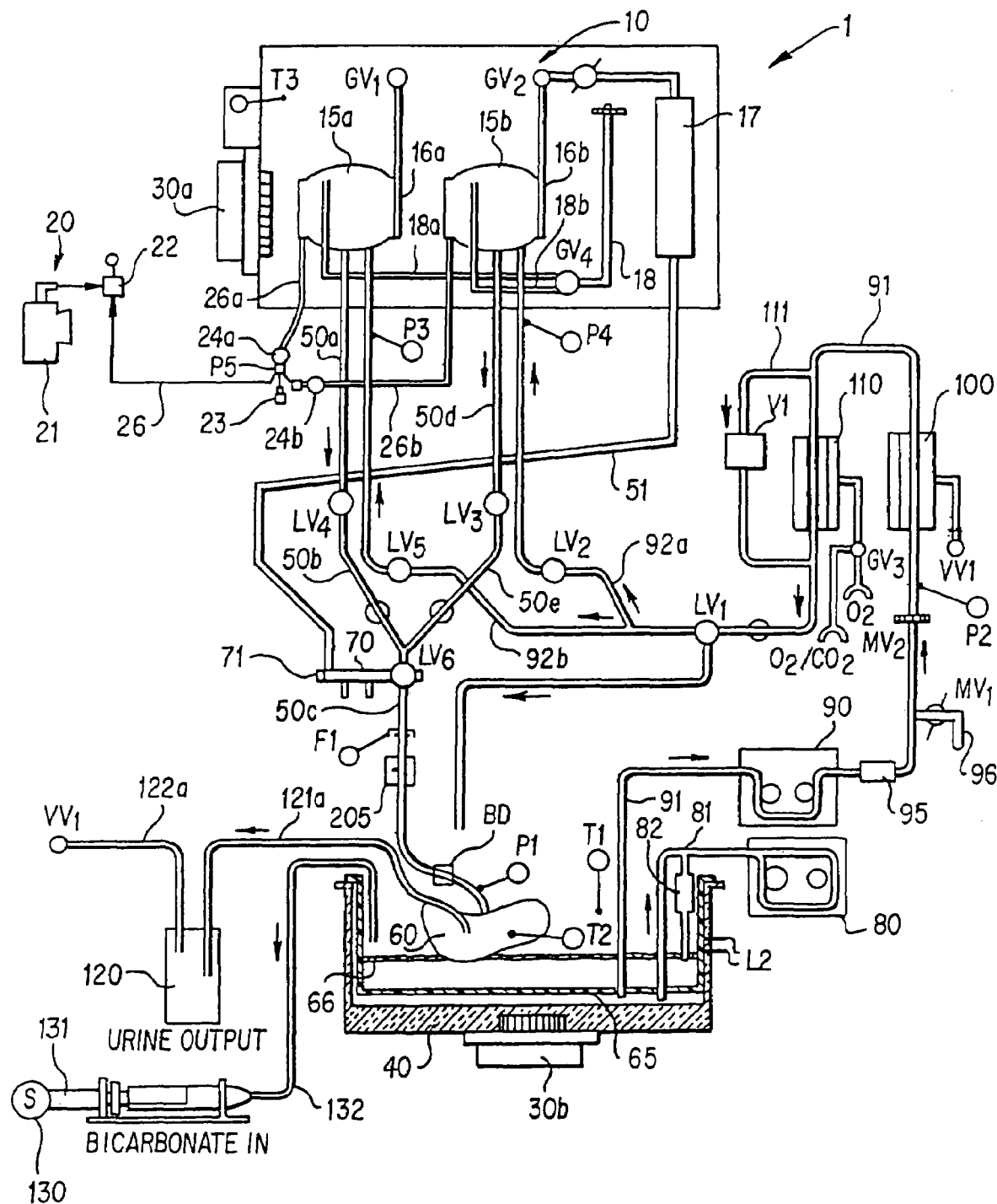
FIG. 2 is a schematic diagram of an apparatus of FIG. 1.
Figure 3:
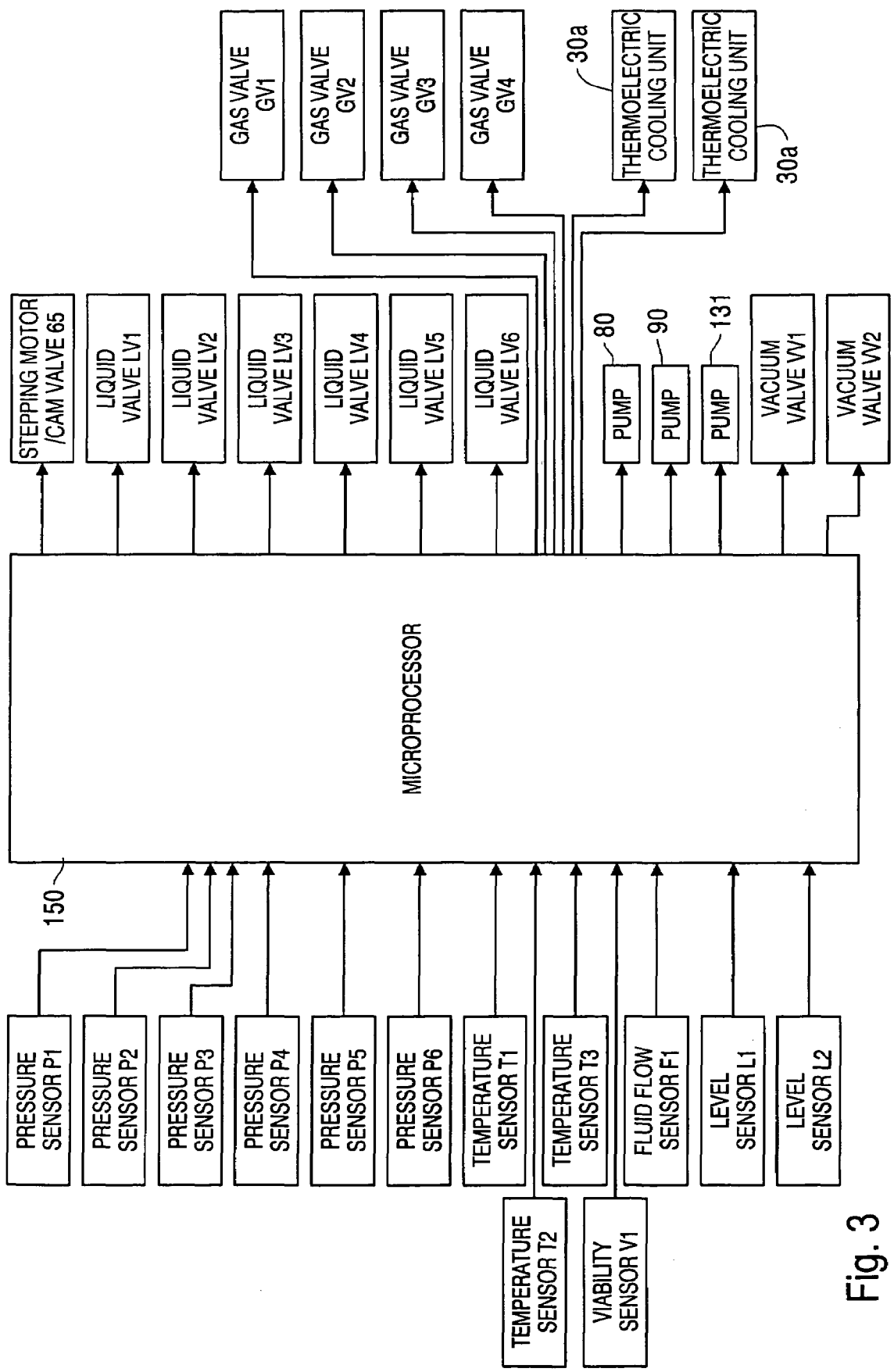
FIG. 3 is a diagram of the electronics of the apparatus of FIG. 2.

FIG. 1 shows an organ perfusion apparatus 1 according to the invention. FIG. 2 is a schematic illustration of the apparatus of FIG. 1. The apparatus 1 is preferably at least partially microprocessor controlled, and pneumatically actuated. A microprocessor 150 connection to the sensors, valves, thermoelectric units and pumps of the apparatus 1 is schematically shown in FIG. 3. Microprocessor 150 and apparatus 1 may be configured to and are preferably capable of further being connected to a computer network to provide data sharing, for example across a local area network or across the Internet.

The organ perfusion apparatus 1 is preferably capable of perfusing one or more organs simultaneously, at both normothermic and hypothermic temperatures (hereinafter, normothermic and hypothermic perfusion modes). All medical fluid contact surfaces are preferably formed of or coated with materials compatible with the medical fluid used, more preferably non-thrombogenic materials. As shown in FIG. 1, the apparatus 1 may include a housing 2 which includes front cover 4, which is preferably translucent, and a reservoir access door 3. The apparatus preferably has one or more control and display areas 5a, 5b, 5c, 5d for monitoring and controlling perfusion.

As schematically shown in FIG. 2, enclosed within the housing 2 is a reservoir 10 which preferably includes three reservoir tanks 15a, 15b, 17. Two of the reservoir tanks 15a, 15b are preferably standard one liter infusion bags, each with a respective pressure cuff 16a, 16b. A pressure source 20 can be provided for pressurizing the pressure cuffs 16a, 16b. The pressure source 20 is preferably pneumatic and may be an on board compressor unit 21 supplying at least 10 LPM external cuff activation via gas tubes 26,26a,26b, as shown in FIG. 2. The invention, however, is not limited to use of an on board compressor unit as any adequate pressure source can be employed, for example, a compressed gas (e.g., air, $CO_2$, oxygen, nitrogen, etc.) tank (not shown) preferably with a tank volume of 1.5 liters at 100 psi or greater for internal pressurization. Alternatively, an internally pressurized reservoir tank (not shown) may be used. Reservoir tanks 15a, 15b, 17 may, in embodiments, be bottles or other suitably rigid reservoirs that can supply perfusate by gravity or can be pressurized by compressed gas.

Gas valves 22-23 may be provided on the gas tube 26 to allow for control of the pressure provided by the onboard compressor unit 21. Anti-back flow valves 24a, 24b may be provided respectively on the gas tubes 26a, 26b. Pressure sensors P5, P6 may be provided respectively on the gas tubes 26a, 26b to relay conditions therein to the microprocessor 150, shown in FIG. 3. Perfusion, diagnostic and/or transporter apparatus may be provided with sensors to monitor perfusion fluid pressure and flow in the particular apparatus to detect faults in the particular apparatus, such as pressure elevated above a suitable level for maintenance of the organ. Gas valves $GV_1$ and $GV_2$ may be provided to release pressure from the cuffs 16a, 16b. One or both of gas valves $GV_1$ and $GV_2$ may be vented to the atmosphere. Gas valve $GV_4$ in communication with reservoir tanks 15a, 15b via tubing 18a, 18b may be provided to vent air from the reservoir tanks 15a, 15b through tubing 18. Tubing 18, 18a, 18b, 26, 26a and/or 26b may be configured with filters and/or check valves to prevent biological materials from entering the tubing or from proceeding further along the fluid path. The check valves and/or filters may be used to prevent biological materials from leaving one organ perfusion tubeset and being transferred to the tubeset of a subsequent organ in a multiple organ perfusion configuration. The check valves and/or filters may also be used to prevent biological materials, such as bacteria and viruses, from being transferred from organ to organ in subsequent uses of the perfusion apparatus in the event that such biological materials remain in the perfusion apparatus after use. The check valves and/or filters may be provided to prevent contamination problems associated with reflux in the gas and/or vent lines. For example, the valves may be configured as anti-reflux valves to prevent reflux. The third reservoir tank 17 is preferably pressurized by pressure released from one of the pressure cuffs via gas valve $GV_2$.

The medical fluid may be blood or a synthetic fluid and may, for example, be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. An oxygenated (e.g., cross-linked hemoglobin-based bicarbonate) solution is preferred for a normothermic mode while a non-oxygenated (e.g., simple crystalloid solution preferably augmented with antioxidants) solution is preferred for a hypothermic mode The specific medical fluids used in both the normothermic and hypothermic modes may be designed or selected to reduce or prevent the washing away of or damage to the vascular endothelial lining of the organ. For a hypothermic perfusion mode, as well as for flush and/or static storage, a preferred solution is the solution disclosed in U.S. Pat. No. 6,492,103, the entire disclosure of which is incorporated herein by reference. Examples of additives which may be used in perfusion solutions for the present invention are also disclosed in U.S. Pat. No. 6,046,046 to Hassanein, the entire disclosure of which is incorporated by reference. Of course, other suitable solutions and materials may be used, as is known in the art.

The medical fluid within reservoir 10 is preferably brought to a predetermined temperature by a first thermoelectric unit 30a in heat transfer communication with the reservoir 10. A temperature sensor T3 relays the temperature within the reservoir 10 to the microprocessor 150, which adjusts the thermoelectric unit 30a to maintain a desired temperature within the reservoir 10 and/or displays the temperature on a control and display areas 5a for manual adjustment. Alternatively or in addition, and preferably where the organ perfusion device is going to be transported, the medical fluid within the hypothermic perfusion fluid reservoir can be cooled utilizing a cryogenic fluid heat exchanger apparatus such as that disclosed in filed U.S. Pat. No. 6,014,864, which is hereby incorporated by reference.

Figure 4A:
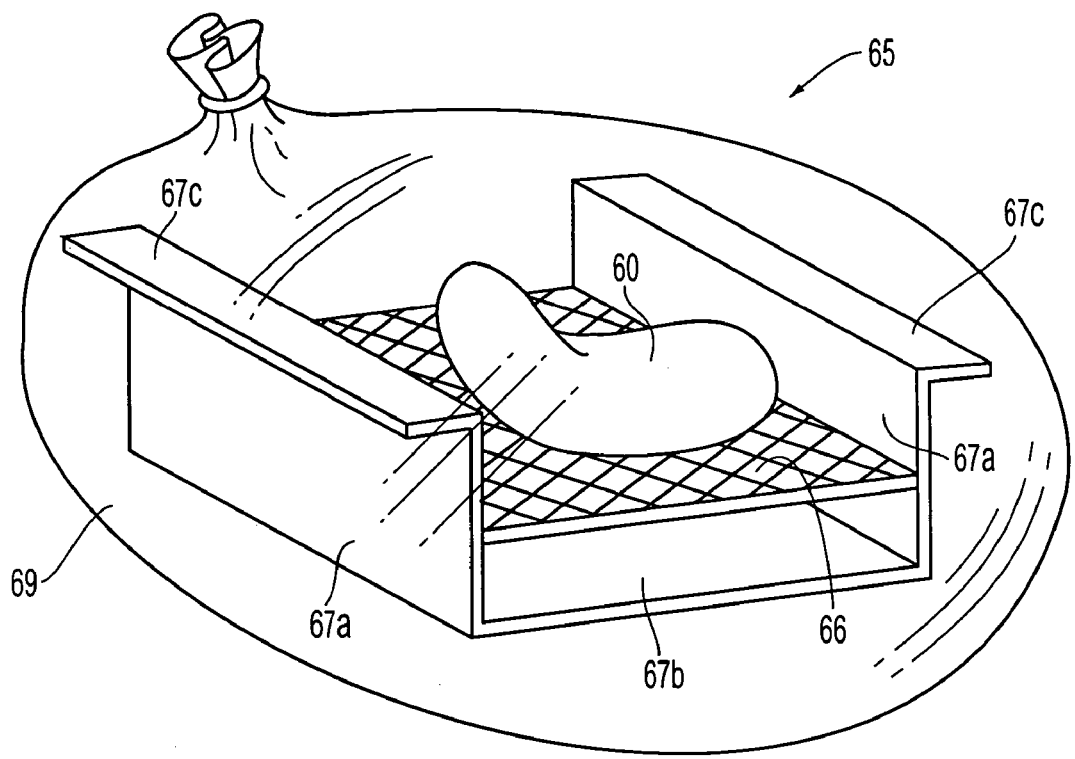
FIGS. 4A-4D show perspective views of various embodiments of an organ cassette according to the invention.
Figure 4B:
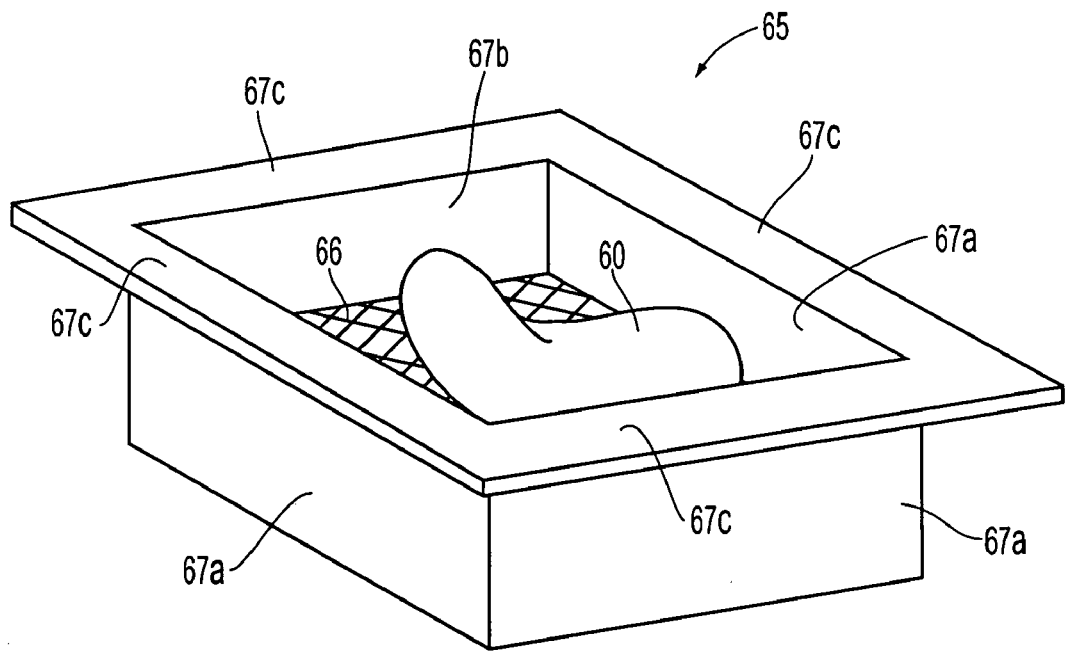
Figure 4C:
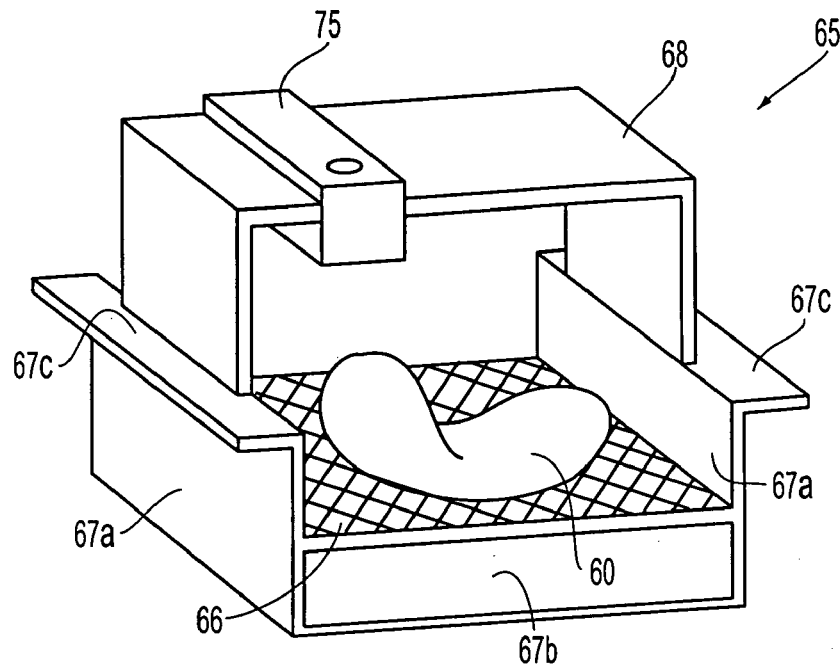
Figure 4D:
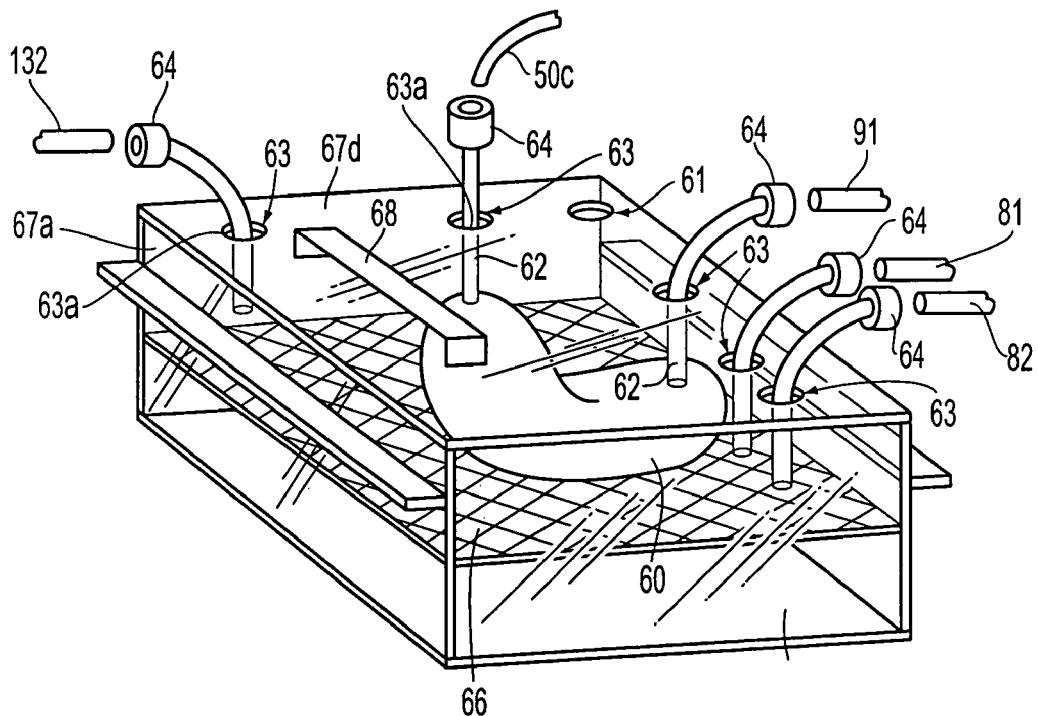
Figure 5:
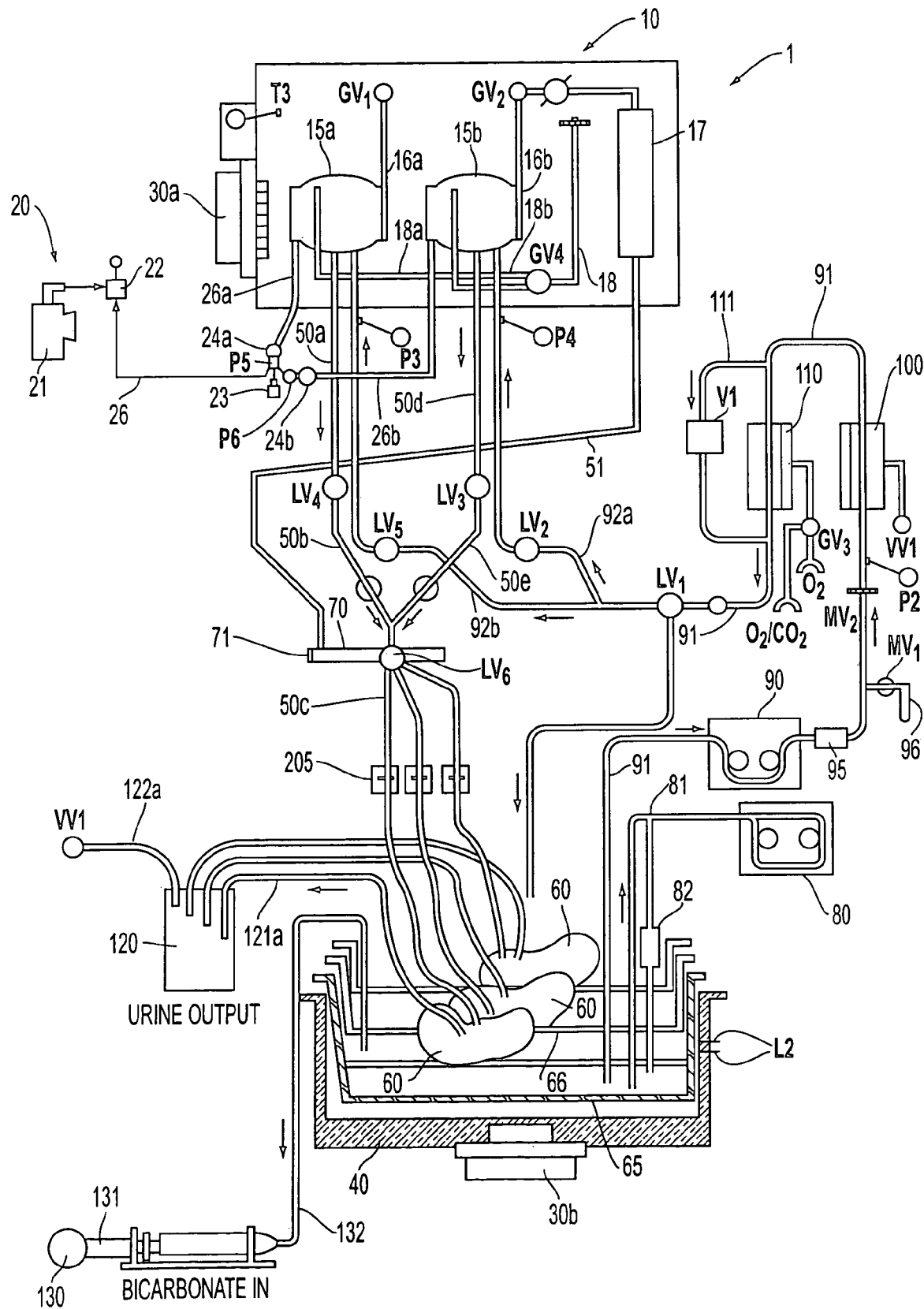
FIG. 5 is a schematic diagram of an organ perfusion apparatus configured to simultaneously perfuse multiple organs.

An organ chamber 40 is provided which supports a cassette 65, as shown in FIG. 2, which holds an organ to be perfused, or a plurality of cassettes 65, as shown in FIG. 5, preferably disposed one adjacent the other. Various embodiments of the cassette 65 are shown in FIGS. 4A-4D. The cassette 65 is preferably formed of a material that is light but durable so that the cassette 65 is highly portable. The material may also be transparent to allow visual inspection of the organ.

FIG. 4A shows a cassette 65 which holds an organ 60 to be perfused. Various embodiments of such a cassette 65 are shown in FIGS. 4A-4D, 6A, 6B, 10 and 12. The cassette 65 is preferably formed of a material that is light but durable so that the cassette 65 is highly portable. The material may also be transparent to allow visual inspection of the organ.

Preferably the cassette 65 includes side walls 67a, a bottom wall 67b and an organ supporting surface 66, which is preferably formed of a porous, perforated or mesh material to allow fluids to pass there through. The cassette 65 may also include a top 67d and may be provided with an opening(s) 63 for tubing (see, for example, FIG. 4D). The opening(s) 63 may include seals 63a (e.g., septum seals or o-ring seals) and optionally be provided with plugs (not shown) to prevent contamination of the organ and maintain a sterile environment. Additionally, the cassette 65 may be provided with tubing for connection to an organ and/or to remove medical fluid from the organ bath, and a connection device(s) 64 for connecting the tubing to, for example, tubing 50c, 81, 82, 91 and/or 132, (see, for example, FIG. 4D) of an organ storage, transporter, perfusion and/or diagnostic apparatus.

The cassette 65, and/or the organ support, opening(s), tubing(s) and/or connections(s), may be specifically tailored to the type of organ and/or size of organ to be perfused. Flanges 67c of the side support walls 67a can be used to support the cassette 65 disposed in an organ storage, transporter, perfusion and/or diagnostic apparatus. The cassette 65 may further include a handle 68 which allows the cassette 65 to be easily handled, as shown, for example, in FIGS. 4C and 4D. Each cassette 65 may also be provided with its own mechanism (e.g., stepping motor/cam valve 75 (for example, in the handle portion 68, as shown in FIG. 4C)) for fine tuning the pressure of medical fluid perfused into the organ 60 disposed therein, as discussed in more detail below. Alternatively, pressure may, in embodiments, be controlled by way of a pneumatic chamber, such as an individual pneumatic chamber for each organ (not shown), or by any suitable variable valve such as a rotary screw valve or a helical screw valve.

Cassette 65 may be provided with a closeable and/or filtered vent 61 (see, for example, FIG. 4D). Vent 61 preferably includes a filter device, and provides for control and/or equalization of pressure within the cassette without contamination of the contents of the cassette. For example, organs are frequently transported by aircraft, in which pressure changes are the norm. Even ground transportation can involve pressure changes as motor vehicles pass through tunnels, over mountains, etc. It is often desirable to provide for pressure equalization of the cassette under such circumstances. However, free flow of air to achieve pressure equalization might introduce contaminants into the cassette. Thus, a filtering vent 61 is preferably provided to allow the air flow without permitting introduction of contaminants into the cassette.

The filter preferably will let clean air pass in both directions but will not allow dirt, dust, liquids and other contaminants to pass. The pore size in the filters can be any size desired and can be small enough to prevent bacteria from passing. A pressure control valve can optionally be associated with vent 61 as well. Such a valve may be configured or controlled to restrict the rate at which external pressure changes are transmitted to the inside of the cassette, or even to prevent pressure increases and/or decreases, as desired.

Figure 6A:
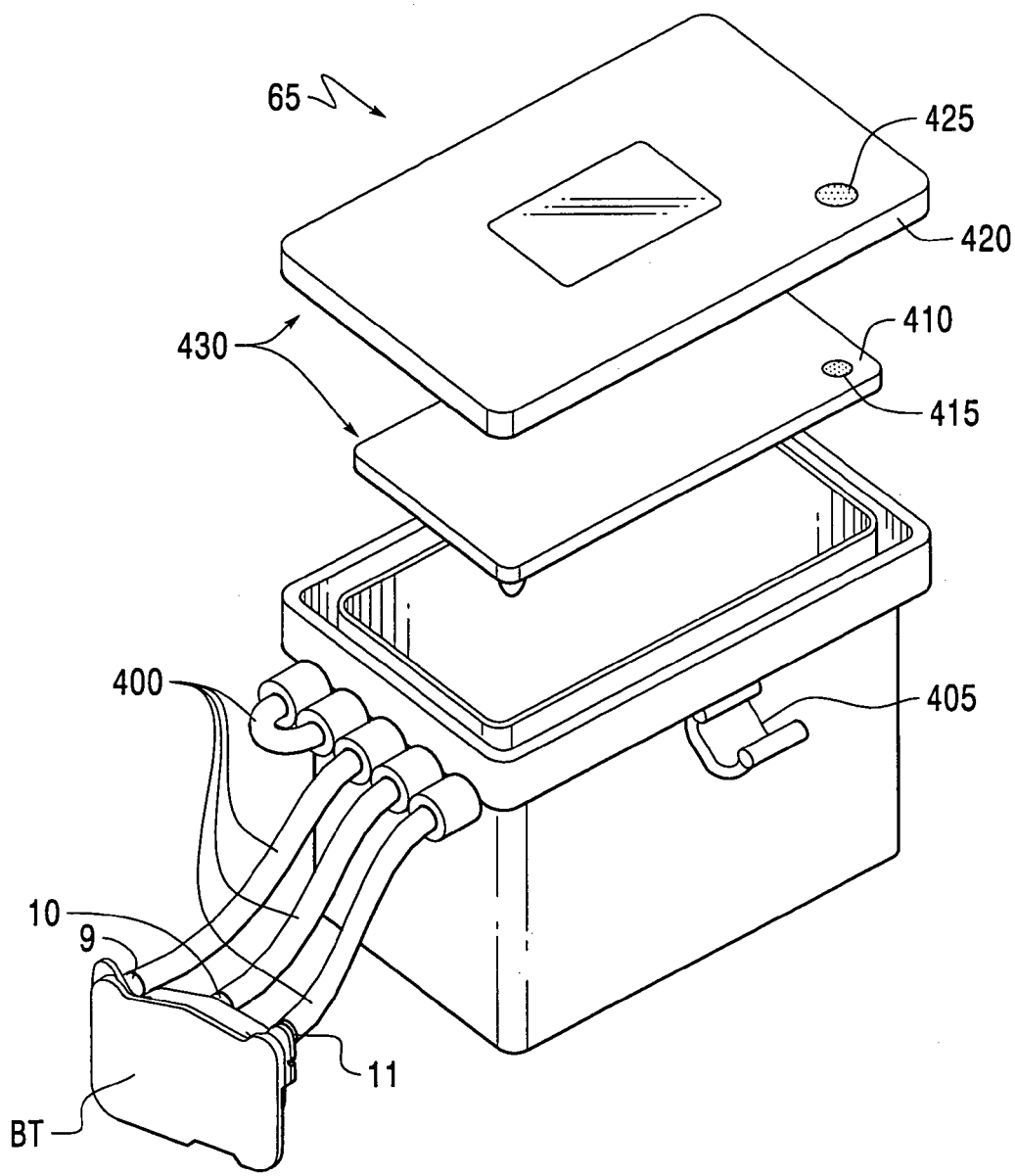
FIGS. 6A and 6B show an embodiment of an organ cassette of the present invention.
Figure 6B:
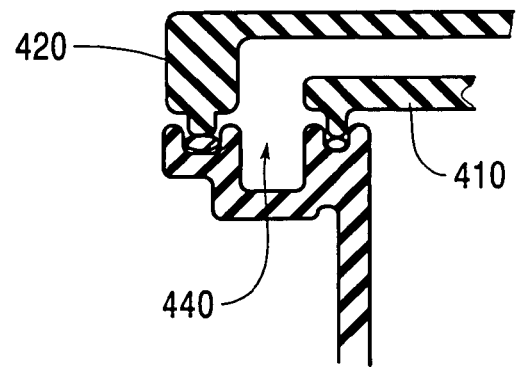

FIGS. 6A-6B show an alternative embodiment of cassette 65. The cassette 65 is a portable device and is provided with a lid, preferably two lids, an inner lid 410 and an outer lid 420. As such, the one or more lids 410 and 420 can create a substantially airtight seal with the cassette 65. This air tight seal can create a pressure difference between the inside and outside of cassette 65. Pressure sensors that control perfusion of the organ may be referenced to the atmospheric pressure. In such embodiments, it is desirable that the air space around the organ in cassette 65 is maintained at atmospheric pressure.

Accordingly, the cassette may also include one or more devices for controlling the pressure. The devices for controlling pressure can be an active or passive device such as a valve or membrane. Membranes 415 and 425, for example, can be located in the inner lid 410 and outer lid 420, respectively. It should be appreciated that any number of membranes can be located in the cassette (including its lid(s)) without departing from the spirit and scope of the invention. The membranes 415 and 425 are preferably hydrophobic membranes which help maintain an equal pressure between the inside and the outside of the cassette. A pressure control valve can optionally be associated with membranes 415 and 425. Such a pressure control valve may be configured or controlled to restrict the rate at which external pressure changes are transmitted to the inside of the cassette, or even to prevent pressure increases and/or decreases, as desired.

The membranes 415 and 425, if sufficiently flexible, can be impermeable or substantially impermeable. Alternatively, they may include filters that will let clean air pass in both directions, however, the membranes 415 and 425 will not allow dirt, dust, liquids and other contaminants to pass. The pore size in the filters can be any size desired, and preferably, the pore size of the membranes 415 and 425 can be small enough to prevent bacteria from passing. The actions of the membranes 415 and 425 and corresponding filters help maintain the sterility of the system.

Preferably, cassette 65 is made of a sufficiently durable material that it can withstand penetration and harsh impact. The lids 410 and 420 may be removable or may be hinged or otherwise connected to the body of cassette 65. Clasp 405, for example, may provide a mechanism to secure lids 410 and 420 to the top of cassette 65. Clasp 405 may additionally be configured with a lock to provide further security and stability. A biopsy and/or venting port 430 may additionally be included in inner lid 410 or both inner lid 410 and outer lid 420. Port 430 may provide access to the organ to allow for additional diagnosis of the organ with minimal disturbance of the organ. Cassette 65 may also have an overflow trough 440 (shown in FIG. 6B as a channel present in the top of cassette 65). When lids 410 and 420 are secured on cassette 65, overflow trough 440 provides a region that is easy to check to determine if the inner seal is leaking. Perfusate may be poured into and out of cassette 65 and may be drained from cassette 65 through a stopcock or removable plug.

In FIG. 6A, cassette 65 is shown with tubeset 400. Tubeset 400 can be connected to perfusion apparatus 1 or to an organ transporter or an organ diagnostic apparatus, and allows cassette 65 to be moved between various apparatus without jeopardizing the sterility of the interior of cassette 65. Preferably, cassette 65 is made of a sufficiently durable material that it can withstand penetration and harsh impact. As shown in FIG. 6A, the tube set may be connected to a bubble trap device BT. A preferred such device is described in detail in a U.S. provisional patent application filed simultaneously herewith entitled "Device for separating bubbles from a liquid path" (attorney docket no. 115624).

Cassette 65 and/or its lid(s) may be constructed of an optically transparent material to allow for viewing of the interior of cassette 65 and monitoring of the organ and to allow for video images or photographs to be taken of the organ. A perfusion apparatus or cassette 65 may be wired and fitted with a video camera or a photographic camera, digital or otherwise, to record the progress and status of the organ. Captured images may be made available over a computer network such as a local area network or the internet to provide for additional data analysis and remote monitoring. Cassette 65 may also be provided with a tag that would signal, e.g., through a bar code, magnetism, radio frequency, or other means, the location of the cassette, that the cassette is in the apparatus, and/or the identity of the organ to perfusion, storage, diagnostic and/or transport apparatus. Cassette 65 may be sterile packaged and/or may be packaged or sold as a single-use disposable cassette, such as in a peel-open pouch. A single-use package containing cassette 65 may also include tubeset 400 and/or tube frame 200, discussed further below.

Cassette 65 is preferably configured such that it may be removed from an organ perfusion apparatus and transported to another organ perfusion and/or diagnostic apparatus in a portable transporter apparatus as described herein or, for example, a conventional cooler or a portable container such as that disclosed in U.S. Pat. No. 6,209,343, or U.S. Pat. No. 5,586,438 to Fahy, both of which are hereby incorporated by reference in their entirety.

In various exemplary embodiments according to this invention, when transported, the organ may be disposed on the organ supporting surface 66 and the cassette 65 may be enclosed in a preferably sterile bag 69, as shown, for example, in FIG. 4A. When the organ is perfused with medical fluid, effluent medical fluid collects in the bag 69 to form an organ bath. Alternatively, cassette 65 can be formed with a fluid tight lower portion in which effluent medical fluid may collect, or effluent medical fluid may collect in another compartment of an organ storage, transporter, perfusion and/or diagnostic apparatus, to form an organ bath. In either case, the bag 69 would preferably be removed prior to inserting the cassette into an organ storage, transporter, perfusion and/or diagnostic apparatus. Further, where a plurality of organs are to be perfused, multiple organ compartments may be provided. Alternatively, cassette 65 can be transported in the cassette and additionally carried within a portable organ transporter.

Figure 7:
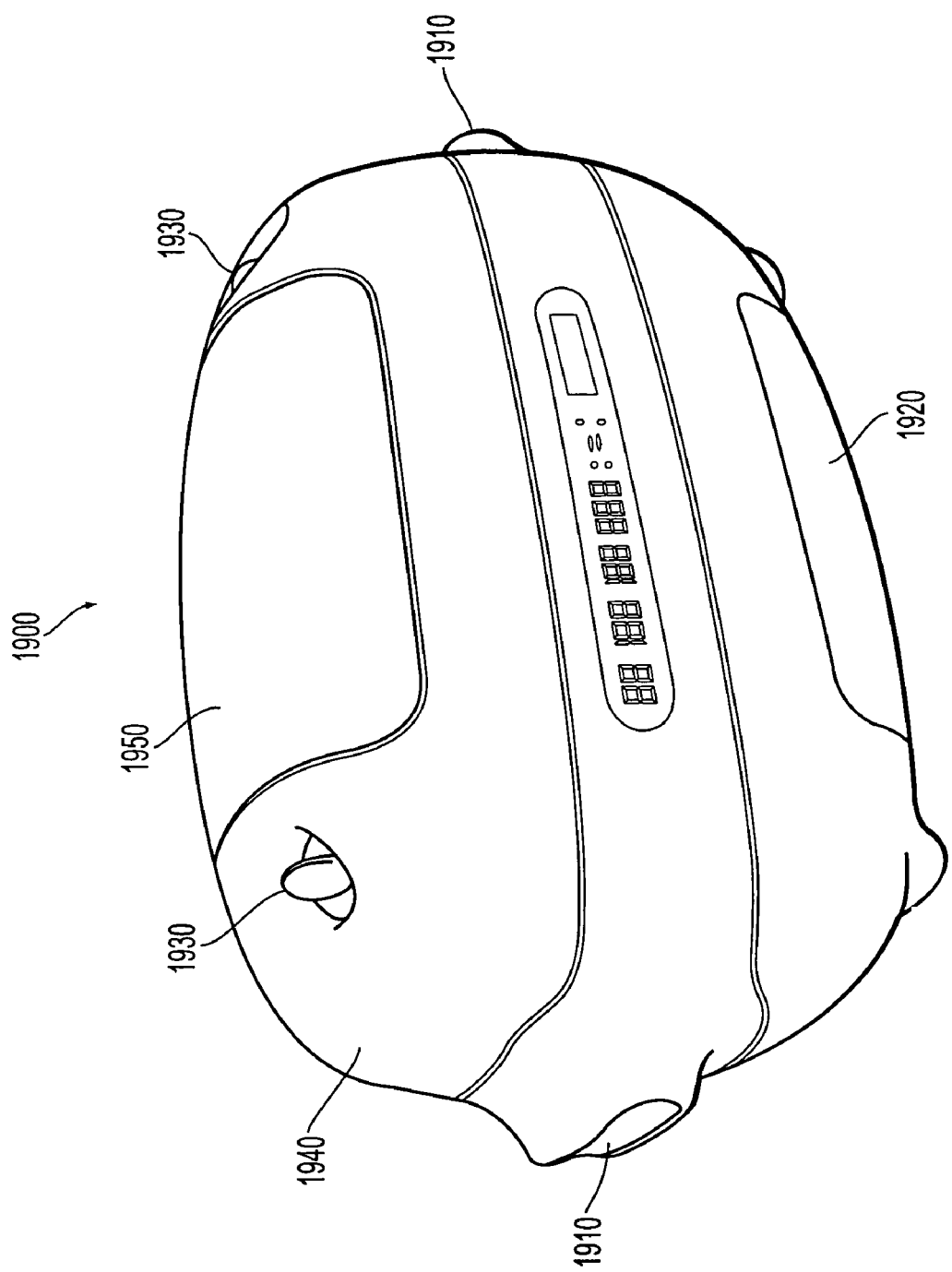
FIG. 7 shows an exterior perspective view of an organ transporter according to the present invention.

FIG. 7 shows an external view of an embodiment of a transporter 1900 of the invention. The transporter 1900 of FIG. 7 has a stable base to facilitate an upright position and handles 1910 for carrying transporter 1900. Transporter 1900 may also be fitted with a shoulder strap and/or wheels to assist in carrying transporter 1900. A control panel 1920 is preferably also provided. Control panel 1920 may display characteristics, such as, but not limited to, infusion pressure, attachment of the tube frame, power on/off, error or fault conditions, flow rate, flow resistance, infusion temperature, bath temperature, pumping time, battery charge, temperature profile (maximums and minimums), cover open or closed, history log or graph, and additional status details and messages, some or all of which are preferably further transmittable to a remote location for data storage and/or analysis. Flow and pressure sensors or transducers in transporter 1900 may be provided to calculate various organ characteristics including pump pressure and vascular resistance of an organ, which can be stored in computer memory to allow for analysis of, for example, vascular resistance history, as well as to detect faults in the apparatus, such as elevated pressure.

Transporter 1900 preferably has latches 1930 that require positive user action to open, thus avoiding the possibility that transporter 1900 inadvertently opens during transport. Latches 1930 hold top 1940 in place on transporter 1900 in FIG. 7. Top 1940 or a portion thereof may be constructed with an optically transparent material to provide for viewing of the cassette and organ perfusion status. Transporter 1900 may be configured with a cover open detector that monitors and displays whether the cover is open or closed. Transporter 1900 may be configured with an insulating exterior of various thicknesses to allow the user to configure or select transporter 1900 for varying extents and distances of transport. In embodiments, compartment 1950 may be provided to hold patient and organ data such as charts, testing supplies, additional batteries, hand-held computing devices and/or configured with means for displaying a UNOS label and/or identification and return shipping information.

Figure 8:
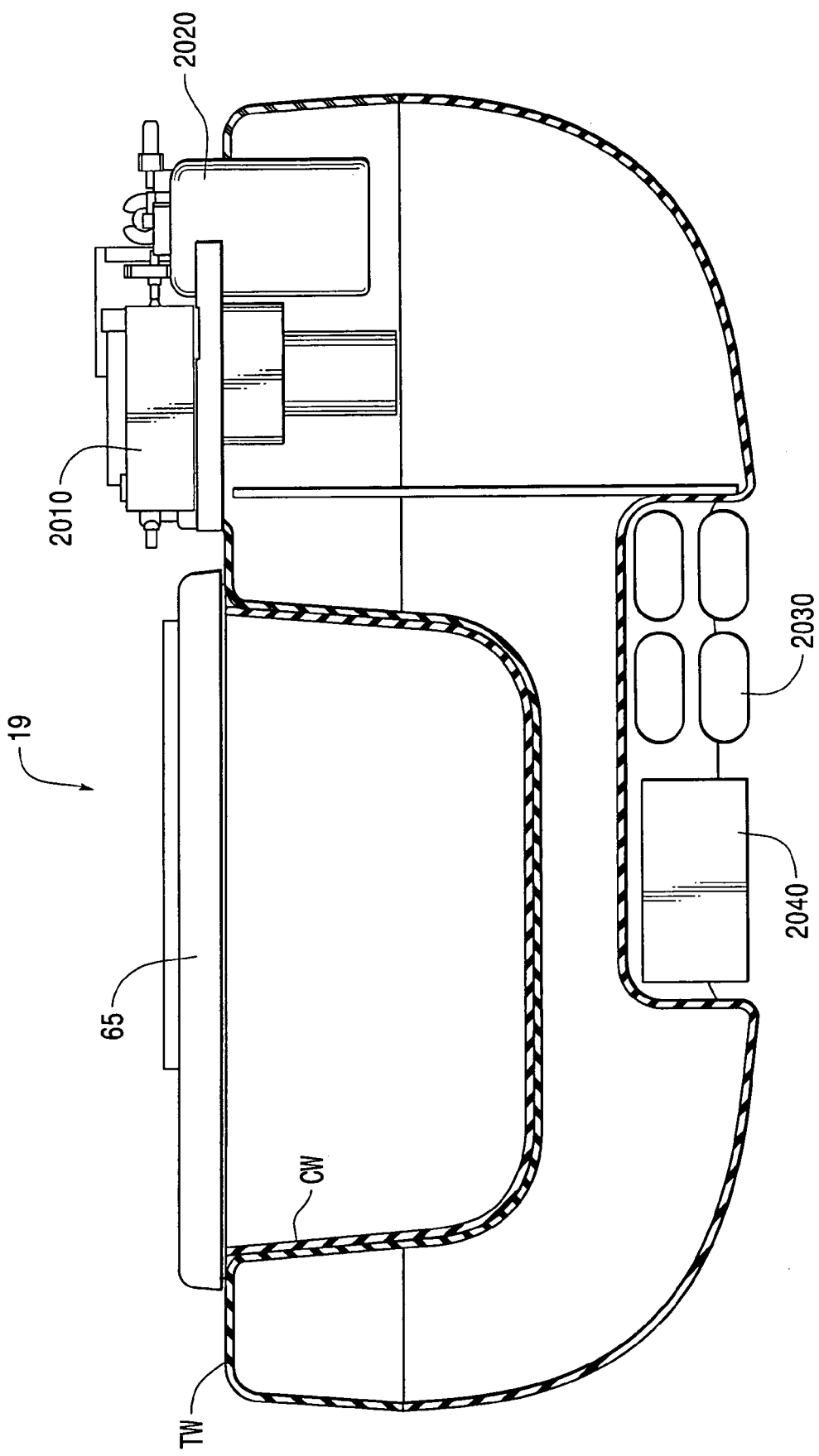
FIG. 8 shows a cross section view of an organ transporter of FIG. 7.

FIG. 8 shows a cross-section view of a transporter 1900. Transporter 1900 contains cassette 65 and pump 2010. Cassette 65 may preferably be placed into or taken out of transporter 1900 without disconnecting tubeset 400 from cassette 65, thus maintaining sterility of the organ. In embodiments, sensors in transporter 1900 can detect the presence of cassette 65 in transporter 1900, and depending on the sensor, can read the organ identity from a barcode or radio frequency or other "smart" tag that may be attached or integral to cassette 65. This can allow for automated identification and tracking of the organ and helps monitor and control the chain of custody. A global positioning system may be added to transporter 1900 and/or cassette 65 to facilitate tracking of the organ. Transporter 1900 may be interfaceable to a computer network by hardwire connection to a local area network or by wireless communication while in transit. This interface may allow data such as perfusion parameters, vascular resistance, and organ identification and transporter and cassette location to be tracked and displayed in real-time or captured for future analysis.

Transporter 1900 also preferably contains a filter 2020 to remove sediment and other particulate matter, preferably ranging in size from 0.05 to 15 microns in diameter or larger, from the perfusate to prevent clogging of the apparatus or the organ. Transporter 1900 preferably also contains batteries 2030, which may be located at the bottom of transporter 1900 or beneath pump 2010 or at any other location but preferably one that provides easy access to change batteries 2030. Batteries 2030 may be rechargeable outside of transporter 1900 or while within transporter 1900 and/or are preferably hotswappable one at a time. Batteries 2030 are preferably rechargeable rapidly and without full discharge. Transporter 1900 may also provide an additional storage space 2040, for example, at the bottom of transporter 1900, for power cords, batteries and other accessories. Transporter 1900 may also include a power port for a DC hookup, e.g., to a vehicle such as an automobile or airplane, and/or for an AC hookup.

As shown in FIG. 8, the cassette wall CW is preferably configured to mate with a corresponding configuration of inner transporter wall TW to maximize contact, and thus heat transfer, there between as discussed in more detail below.

Figure 9:
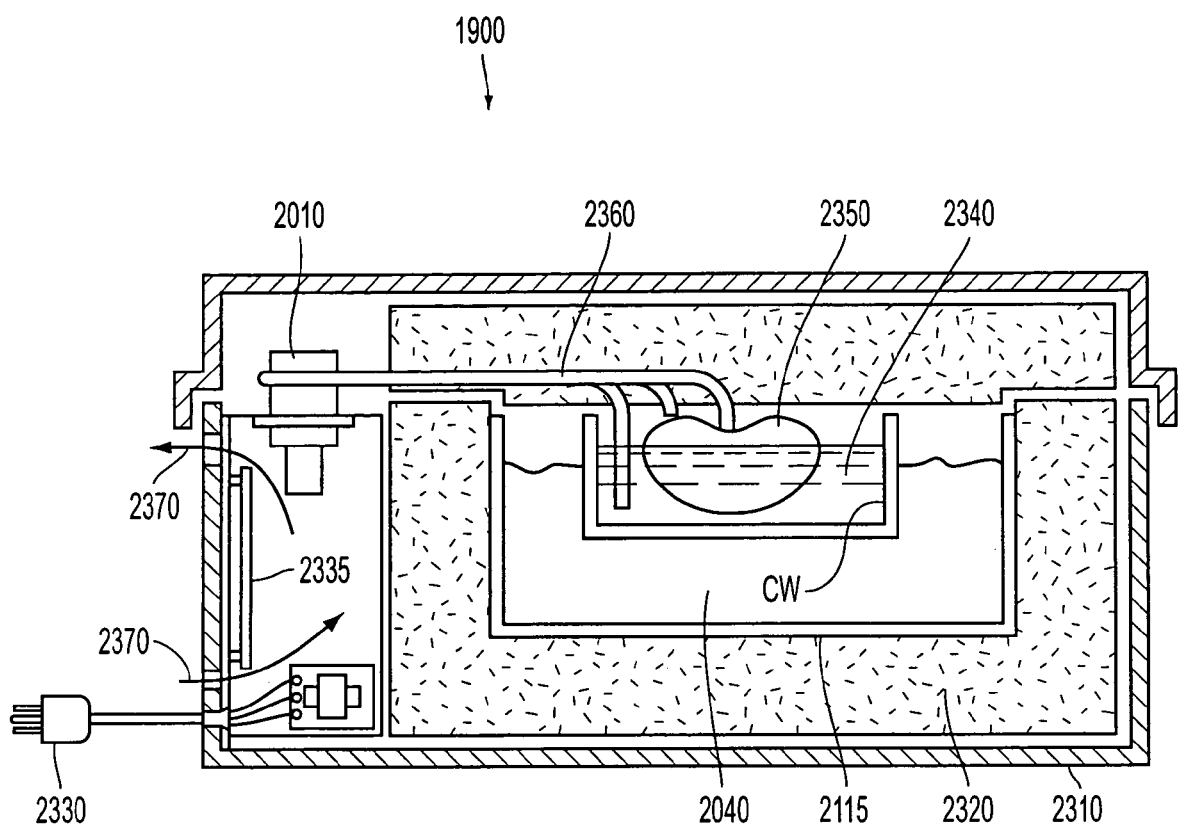
FIG. 9 shows an alternative cross-section view of an organ transporter of FIG. 7.

FIG. 9 shows an alternative cross-section of transporter 1900. In FIG. 9, the transporter 1900 may have an outer enclosure 2310 which may, for example, be constructed of metal, or preferably a plastic or synthetic resin that is sufficiently strong to withstand penetration and impact. Transporter 1900 contains insulation 2320, preferably a thermal insulation made of, for example, glass wool or expanded polystyrene. Insulation 2320 may be various thicknesses ranging from 0.5 inches to 5 inches thick or more, preferably 1 to 3 inches, such as approximately 2 inches thick. Transporter 1900 may be cooled by coolant 2110, which may be, e.g., an ice and water bath or a cryogenic material. In embodiments using cryogenic materials, the design should be such that organ freezing is prevented. An ice and water mixture is preferably an initial mixture of approximately 1 to 1, however, in embodiments the ice and water bath may be frozen solid. Transporter 1900 can be configured to hold various amounts of coolant, preferably up to 10 to 12 liters. An ice and water bath is preferable because it is inexpensive and generally can not get cold enough to freeze the organ. Coolant 2110 preferably lasts for a minimum of 6 to 12 hours and more preferably lasts for a minimum of 30 to 50 hours without changing coolant 2110. The level of coolant 2110 may, for example, be viewed through a transparent region of transporter 1900 or be automatically detected and monitored by a sensor. Coolant 2110 can preferably be replaced without stopping perfusion or removing cassette 65 from transporter 1900. Coolant 2110 is preferably maintained in a watertight compartment 2115 of transporter 1900. For example, an inner transporter wall TW as shown in FIG. 8 can be interposed between the coolant 2110 and cassette wall (CW) in the apparatus of FIG. 9. Compartment 2115 preferably prevents the loss of coolant 2110 in the event transporter 1900 is tipped or inverted. Heat is conducted from the walls of the perfusate reservoir/cassette 65 into coolant 2110 enabling control within the desired temperature range. Coolant 2110 is a failsafe cooling mechanism because transporter 1900 automatically reverts to cold storage in the case of power loss or electrical or computer malfunction. Transporter 1900 may also be configured with a heater to raise the temperature of the perfusate.

Transporter 1900 may be powered by batteries or by electric power provided through plug 2330. An electronics module 2335 may also be provided in transporter 1900. Electronics module 2335 may be cooled by vented air convection 2370, and may further be cooled by a fan. Preferably, electronic module 2335 is positioned separate from the perfusion tubes to prevent the perfusate from wetting electronics module 2335 and to avoid adding extraneous heat from electronics module 2335 to the perfusate. Transporter 1900 preferably has a pump 2010 that provides pressure to perfusate tubing 2360 (e.g. of tube set 400) to deliver perfusate 2340 to organ 2350. Transporter 1900 may be used to perfuse various organs such as a kidney, heart, liver, small intestine and lung. Transporter 1900 and cassette 65 may accommodate various amounts to perfusate 2340, for example up to 3 to 5 liters. Preferably, approximately 1 liter of a hypothermic perfusate 2340 is used to perfuse organ 2350.

Cassette 65 and transporter 1900 are preferably constructed to fit or mate such that efficient heat transfer is enabled. Preferably, the transporter 1900 contains a compartment 2115 for receiving the cassette. The transporter 1900 preferably relies on conduction to move heat from the cassette 65 to coolant 2110 contained in compartment 2115. This movement of heat allows the transporter 1900 to maintain a desired temperature of the perfusion solution. The geometric elements of cassette 65 and transporter 1900 are preferably constructed such that when cassette 65 is placed within transporter 1900, the contact area between cassette 65 and transporter 1900 is as large as possible and they are secured for transport.

Figure 10:
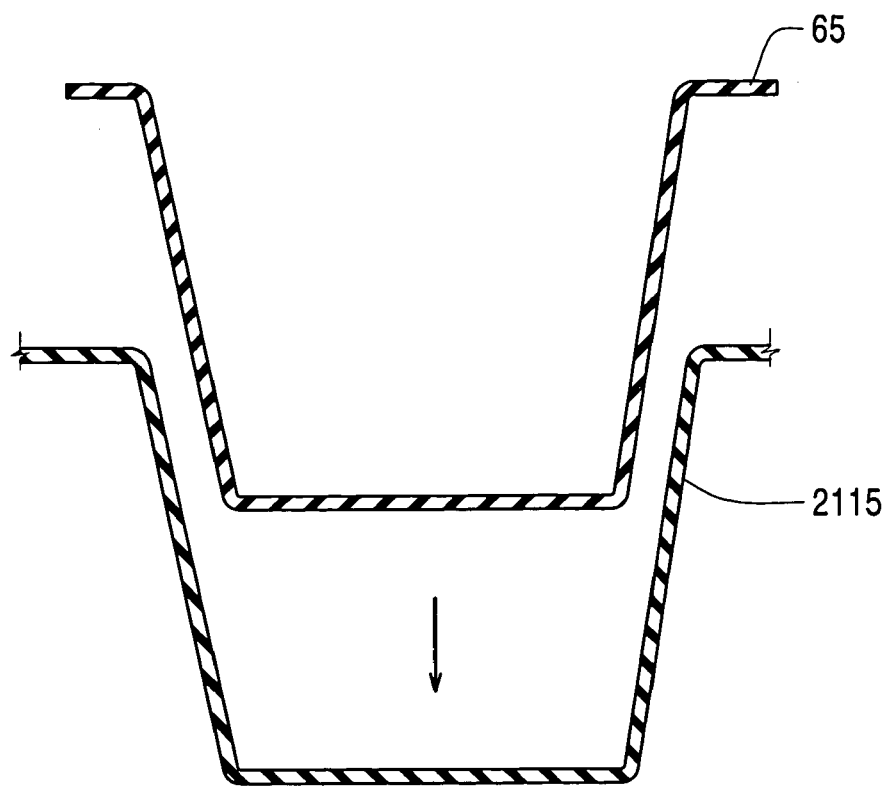
FIG. 10 shows the mating of a cassette with a compartment according to the present invention.
Figure 10:
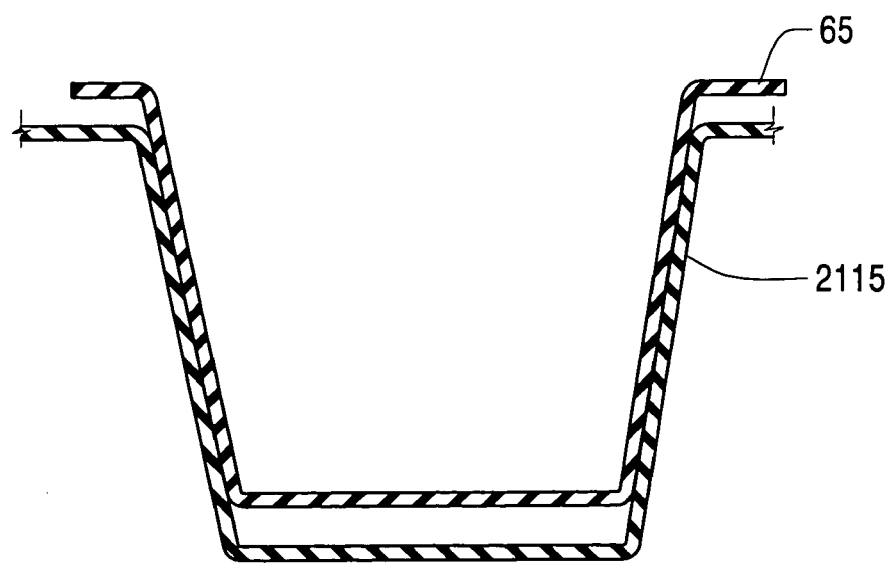

FIG. 10 shows an example of this geometry between cassette 65 and compartment 2115 containing coolant 2110. The interface geometry between cassette 65 and compartment 2115 is preferably designed so that cassette 65 will wedge into a cavity created by compartment 2115. Accordingly, the angles of the side walls are substantially equal and thus, all side walls of cassette 65 make contact with the side walls of compartment 2115 regardless of the shape of the cassette sides or compartment sides, such as flat or curved. Having the included angles substantially equal allows the surfaces of cassette 65 and the compartment 2115 to make contact even when influenced by the thermal expansion and contraction of the walls and mechanical tolerances.

The height of cassette 65 above compartment 2115 is determined by the mating surfaces of cassette 65 and compartment 2115. As shown in FIG. 10 the bottom of the cassette does not have to rest on the bottom of compartment 2115, but can rest at the bottom in embodiments in which the shape of cassette 65 and compartment 2115 allow it. It should be appreciated that the shape of cassette 65 and compartment 2115 in these embodiments can be any shape, such as for example a truncated cone, that allows for maximum contact and therefore maximum heat transfer between them.

As discussed above, heat is conducted from the walls of the perfusate reservoir/cassette 65 into coolant 2110 of compartment 2115 enabling control within the desired temperature range. Coolant 2110 can provide a failsafe cooling mechanism because transporter 1900 automatically reverts to cold storage in the case of power loss or electrical or computer malfunction. Transporter 1900 may also be configured with a heater to raise the temperature of the perfusate.

Figure 11:
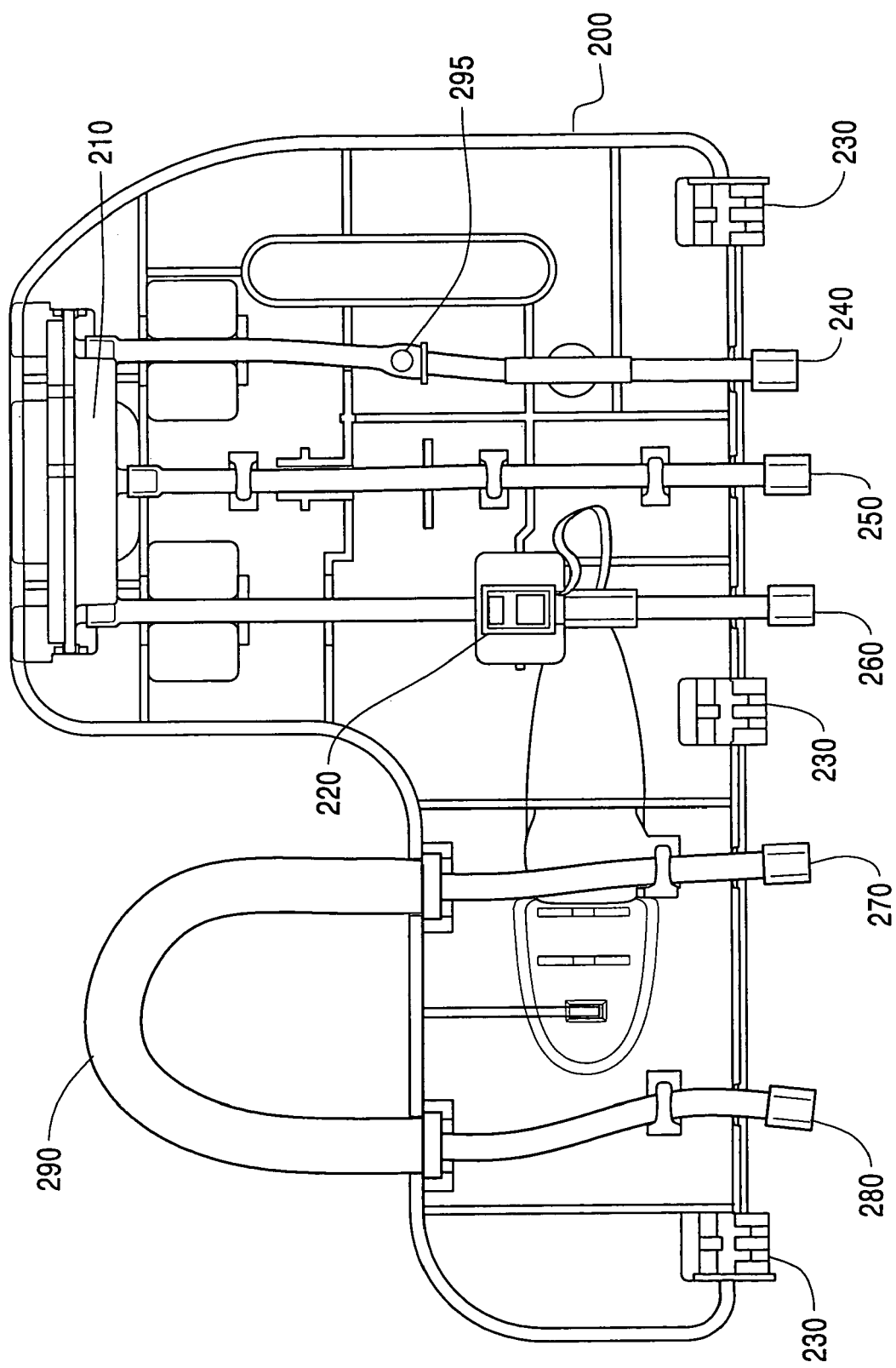
FIG. 11 shows a tube frame with a tube set according to the present invention.
Figure 12:
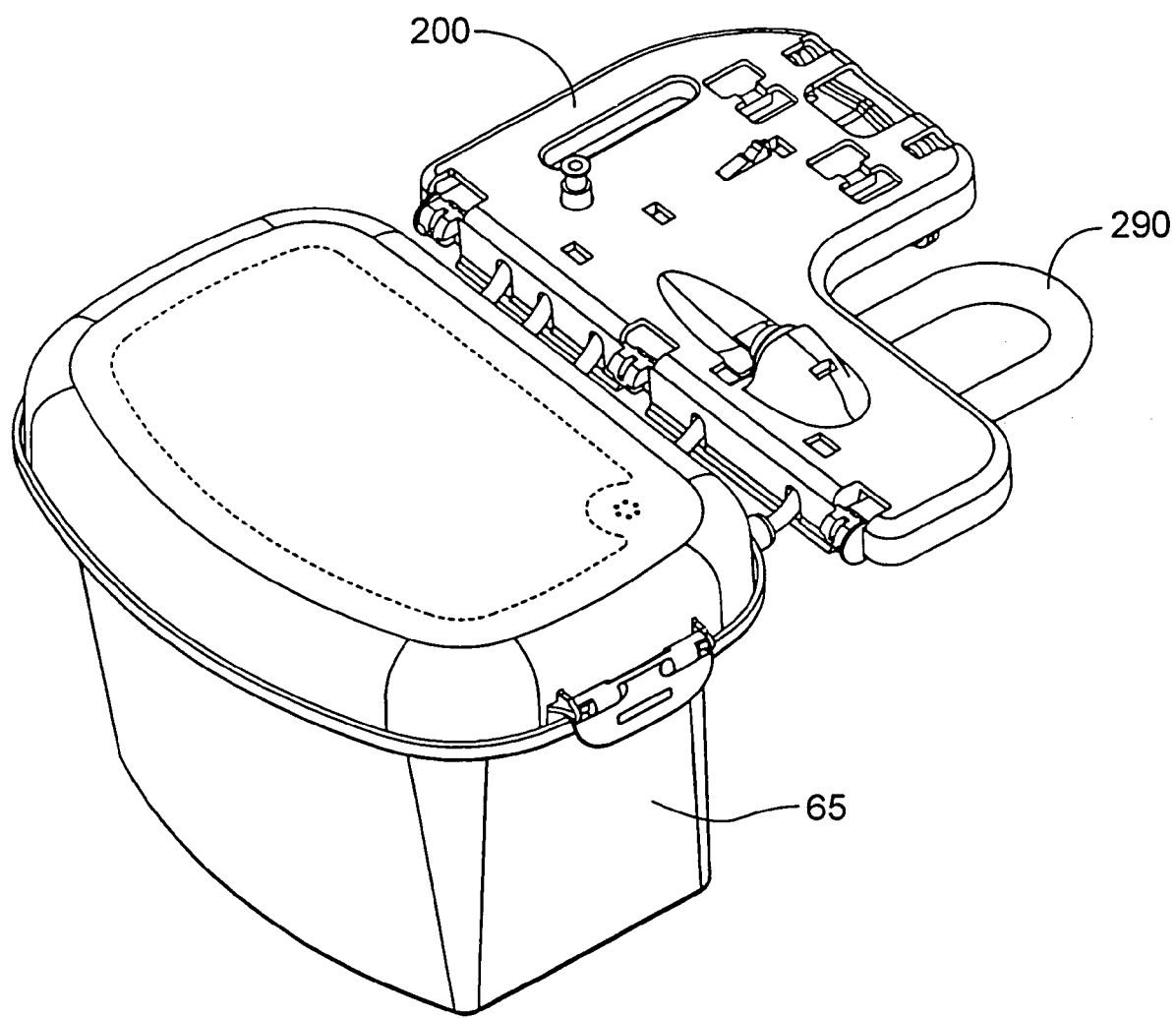
FIG. 12 shows a tube frame connected to a cassette according to the present invention.

FIG. 11 shows a tube frame 200 of embodiments of the invention, which may be used for holding tube set 400 discussed with respect to FIG. 6A. Tube frame 200 is preferably formed of a material that is light but durable, such as for example plastic, so that tube frame 200 is highly portable. The tube frame 200 is designed to hold the tubing of the tube set 400 in desired positions. In FIG. 11, tube frame 200 is shown holding the tubes of tube set 400 of FIG. 6A. It should be appreciated that there may be other numbers of tubes that comprise tube set 400. Having the tubing in set positions allows for easier installation and connection with devices such as cassette 65 as shown in FIG. 12. The cassette 65 and tube frame 200 are then preferably mated with transporter 1900.

When tube frame 200 is mated with cassette 65, the tube set 400 is preferably already connected with the cassette 65. For example, tube 270 provides an inlet to a pump 2010 from the stored liquid at the bottom of cassette 65. The liquid travels through tube 290 and back out outlet 280 through a filter which may, for example, be located inside or outside, for example, below, cassette 65. After traveling through the filter, the liquid will travel to tube 240 and into the bubble trap 210. A sample port 295 may be provided with tube frame 200 to allow for drawing liquid out of or injecting liquid into the tube 240. Liquid travels into the bubble trap 210 in tube 240 and travels out of bubble trap 210 in tube 260, which carries the liquid into the cassette, for example, to infuse and/or wash the organ. Tube 250 will carry liquid or gas leaving the bubble trap 210 into cassette 65 bypassing infusion of, but optionally washing, the organ.

It should be appreciated that tube frame 200 can hold other devices in addition to tubes. For example, tube frame 200 can hold a bubble trap device 210 and a pressure sensor 220 used to control pump 2010. It should also be appreciated that tube frame 200 and tube set 400 can be connected to a variety of devices such as the organ perfusion device 1 or an organ diagnostic device, as well as a cassette and/or transporter.

In various exemplary embodiments, tube frame 200 is preferably attachable to a portion of the transporter 1900. The tube frame 200 may be connected to transporter 1900, and other devices, by way of snaps 230 or other structure that will securely hold the tube frame to the device. Sensors, for example mechanical or electrical sensors, in transporter 1900, or other devices, can be provided to detect the presence of tube frame 200 in transporter 1900. If the tube frame 200 is not properly attached to the transporter, the sensors may be configured to send an appropriate alert message to control panel 1920 for notifying the user of a problem. If no action is taken to properly attach tube frame 200 in a given amount of time automatically set or programmed by the user, transporter 1900 can be programmed to prevent the beginning of perfusion. It should be appreciated that if perfusion has begun and tube frame 200 is not appropriately set, the transporter can be programmed to stop perfusion.

Another valuable feature of the tube frame is that makes the stationary surface for the tube 250, and tube 260. These tubes are used to route perfusion solution either directly to the organ or, bypassing the organ, into the reservoir. It is desirable to have tube 250 and tube 260 located in a relatively fixed position so that the routing may be done by pinching the tubing so that no liquid can pass. The tubes may, for example, be pinched by a solenoid (not shown) located on transporter 1900 that drives a blade that pinches tube 250 and/or tube 260 against the tube frame 200.

While the invention has been described in conjunction with specific embodiments thereof, it is evident that many alternatives, modifications and variations may be apparent to those skilled in the art. Accordingly, the embodiments of the invention as set forth herein are intended to be illustrative, not limiting. Various changes may be made without departing from the spirit and scope of the invention.

What is claimed is:

1. Apparatus for holding an organ or a tissue for at least one of perfusion, storage, diagnosis and transport of the organ or tissue, comprising:
    an organ or tissue transporter being configured to perfuse an organ or a tissue;
    a portable housing having one or more heat transfer surfaces;
    a compartment within the transporter having one or more heat transfer surfaces arranged on an outer surface of the compartment to transfer heat between a cooling source contained within the compartment and at least a part of one of the one or more heat transfer surfaces of the portable housing, the compartment being liquid-tight and preventing contact between a liquid contained within the compartment and the portable housing; and
    an organ or tissue supporting surface configured to support the organ or tissue within said portable housing,
    wherein the portable housing is configured to be received by the transporter and wherein at least a portion of at least one of the one or more heat transfer surfaces of the compartment is in contact with at least a portion of at least one of the one or more heat transfer surfaces of the portable housing to allow effective heat transfer to or from the contents of the portable housing.

2. The apparatus of claim 1, wherein the cooling source is a cooling fluid.

3. The apparatus of claim 2, wherein the cooling fluid is a cryogenic fluid.

4. The apparatus of claim 3, wherein the cryogenic fluid is at least one of ice, water, and a combination of water and ice.

5. The apparatus of claim 1, wherein the supporting surface is configured to support the organ or tissue while allowing effluent medical fluid to pass through said organ or tissue.

6. The apparatus of claim 1, wherein the outer surface of compartment and the portable housing have substantially complementary configurations.

7. The apparatus of claim 6, wherein a majority of at least one of the one or more heat transfer surfaces of the compartment is in contact with a majority of at least one of the one or more heat transfer surfaces of the portable housing.

8. The apparatus of claim 6, wherein substantially all of at least one of the one or more heat transfer surfaces of the compartment is in contact with substantially all of at least one of the one or more heat transfer surfaces of the portable housing.

9. The apparatus of claim 6, wherein the portable housing is configured to mate with the compartment.

10. The apparatus of claim 6, wherein each of the compartment and the portable housing have multiple heat transfer surfaces forming the outer surface of compartment and the portable housing, wherein the multiple heat transfer surfaces of each of the compartment and the portable housing are arranged such that a side cross-sectional view forms a trapezoid.

11. The apparatus of claim 6, wherein the outer surface of the compartment and the portable housing have complementary configurations forming a truncated cone.

12. The apparatus of claim 6, wherein the one or more heat transfer surfaces of the compartment and the one or more heat transfer surfaces of the portable housing are planar surfaces.

13. The apparatus of claim 6, wherein the one or more heat transfer surfaces of the compartment and the one or more heat transfer surfaces of the portable housing are non-planar surfaces.

14. The apparatus of claim 1, wherein the portable housing includes openings configured to allow tubing to pass through said openings and be connected to the organ.

15. The apparatus of claim 14, wherein the tubing can pass through the openings when the portable housing is mated with the compartment.

16. The apparatus of claim 14, wherein the tubing is configured to be mated with the portable housing, when the portable housing is removed from the compartment.

17. The apparatus of claim 1, wherein the transporter includes a heater.

18. The apparatus of claim 1, wherein the portable housing includes a handle that is accessible when the portable housing is mated with the compartment.

19. The apparatus of claim 1, wherein a bottom portion of the portable housing is liquid-tight and configured to collect medical fluid that has passed through a perfused organ to form an organ bath.

20. The apparatus of claim 1, wherein the transporter includes at least one sensor configured to detect a presence of the portable housing within the compartment.

21. A method of transporting an organ or a tissue, comprising:
placing the organ or tissue in a portable housing, the portable housing having one or more heat transfer surfaces;
placing the portable housing containing the organ or tissue in a compartment of a transporter configured to receive the portable housing and configured to perfuse the organ or tissue, the compartment having one or more heat transfer surfaces arranged on an outer surface of the compartment, the compartment being liquid-tight and preventing contact between a liquid contained within the compartment and the portable housing,
wherein at least a portion of at least one of the one or more heat transfer surfaces of the compartment is in contact with at least a portion of at least one of the one or more heat transfer surfaces of the portable housing;
transferring heat between a cooling source contained within the compartment, via at least a part of one of the one or more heat transfer surfaces of the compartment, to or from the contents of the portable housing; and
transporting the organ in said portable housing in said transporter.

22. The method of claim 21, further comprising placing the portable housing containing the organ in an organ or tissue diagnostic device configured to receive the portable housing; and diagnosing the organ or tissue without removal of the organ from the portable housing.

23. The method of claim 21, further comprising placing the portable housing containing the organ or tissue in a perfusion device configured to receive the portable housing; and perfusing the organ or tissue without removal of the organ from the portable housing.

24. The method of claim 21, further comprising connecting tubing to the organ.

25. The method of claim 21, wherein the cooling source is a cooling fluid.

26. The method of claim 25, wherein the cooling fluid is a cryogenic fluid.

27. The method of claim 26, wherein the cryogenic fluid is at least one of ice, water, and a combination of ice and water.

28. The method of claim 25, wherein a bottom portion of the housing is liquid-tight and configured to collect medical fluid that has passed through a perfused organ to form an organ bath.

29. The method of claim 28, further comprising cooling the medical fluid with the cooling fluid.

30. The method of claim 21, wherein the outer surface of the compartment and the portable housing have substantially complementary configurations.

31. The method of claim 30, wherein each of the compartment and the portable housing have multiple heat transfer surfaces forming the outer surface of the compartment and the portable housing, wherein the multiple heat transfer surfaces of each of the compartment and the portable housing are arranged such that a side cross-sectional view forms a trapezoid.

32. The method of claim 30, wherein the outer surface of the compartment and the portable housing have complementary configurations forming a truncated cone.

33. The method of claim 21, wherein the portable housing includes tubing and connection devices to allow connection of an organ in the portable housing to tubing of at least one of the transporter, the organ diagnosis device and the organ perfusion device.

34. The method of claim 21, wherein the portable housing includes a handle and the handle is accessible when the portable housing is mated with the compartment.

35. The method of claim 21, wherein the one or more heat transfer surfaces of the compartment and the one or more heat transfer surfaces of the portable housing are planar surfaces.

36. The method of claim 21, wherein the one or more heat transfer surfaces of the compartment and the one or more heat transfer surfaces of the portable housing are non-planar surfaces.

37. The method of claim 21, wherein the portable housing includes openings configured to allow tubing to pass through said openings and be connected to the organ.

38. The method of claim 37, wherein the tubing can pass through the openings when the portable housing is mated with the compartment.

39. The method of claim 21, wherein the transporter includes a heater to heat the cooling source.

40. The method of claim 39, further comprising transferring heat from the cooling source to the medical fluid.

41. The method of claim 21, wherein the transporter includes at least one sensor configured to detect a presence of the portable housing within the compartment.

42. A system for holding an organ or tissue for transport of the organ or tissue, comprising:
an organ or tissue transporter;
a portable housing having one or more heat transfer surfaces;
a compartment within the transporter having one or more heat transfer surfaces arranged on an outer surface of the compartment to transfer heat between a cooling source contained within the compartment and at least a part of one of the one or more heat transfer surfaces of the portable housing, the compartment being liquid-tight and preventing contact between a liquid contained within the compartment and the portable housing; and
an organ or tissue supporting surface configured to support an organ or tissue within said portable housing;
wherein the portable housing is configured to be received by the transporter and wherein at least a portion of at least one of the one or more heat transfer surfaces of the compartment is in contact with at least a portion of at least one of the one or more heat transfer surfaces of the portable housing to allow effective heat transfer to or from the contents of the portable housing,
wherein the portable housing includes openings configured to allow tubing to pass through said openings and be connected to the organ, the tubing being configured to pass through the openings when the portable housing is mated with the compartment and being configured to be mated with the portable housing when the portable housing is removed from the compartment, and
wherein the portable housing includes a handle that is accessible when the portable housing is mated with the compartment.

43. The system of claim 42, wherein the cooling source is a cooling fluid.

44. The system of claim 43, wherein the cooling fluid is a cryogenic fluid.

45. The system of claim 44, wherein the cryogenic fluid is at least one of ice, water, and a combination of water and ice.

46. The system of claim 42, wherein the supporting surface is configured to support the organ or tissue while allowing effluent medical fluid to pass through said organ or tissue.

47. The system of claim 42, wherein the outer surface of the compartment and the portable housing have substantially complementary configurations.

48. The system of claim 47, wherein a majority of at least one of the one or more heat transfer surfaces of the compartment is in contact with a majority of at least one of the one or more heat transfer surfaces of the portable housing.

49. The system of claim 47, wherein substantially all of at least one of the one or more heat transfer surfaces of the compartment is in contact with substantially all of at least one of the one or more heat transfer surfaces of the portable housing.

50. The system of claim 47, wherein the portable housing is configured to mate with the outer surface of the compartment.

51. The system of claim 47, wherein each of the compartment and the portable housing have multiple heat transfer surfaces forming the outer surface of the compartment and the portable housing, wherein the multiple heat transfer surfaces of each of the compartment and the portable housing are arranged such that a side cross-sectional view forms a trapezoid.

52. The system of claim 47, wherein the outer surface of the compartment and the portable housing have complementary configurations forming a truncated cone.

53. The system of claim 47, wherein the one or more heat transfer surfaces of the compartment and the one or more heat transfer surfaces of the portable housing are planar surfaces.

54. The system of claim 47, wherein the one or more heat transfer surfaces of the compartment and the one or more heat transfer surfaces of the portable housing are non-planar surfaces.

55. The system of claim 42, wherein the transporter includes a heater.

56. The system of claim 42, wherein a bottom portion of the portable housing is liquid-tight and configured to collect medical fluid that has passed through a perfused organ to form an organ bath.

57. The system of claim 42, further comprising:
at least one of an organ perfusion device and an organ diagnostic device, wherein the portable housing is configured to be received by the at least one organ perfusion device and the organ diagnostic device and to allow at least one of perfusion and diagnosis of the organ without removal of the organ from the portable housing.

58. The system of claim 42, wherein the transporter includes at least one sensor configured to detect a presence of the portable housing within the compartment.

59. The system of claim 58,
wherein the portable housing includes identification information, and
wherein the sensor identifies the portable housing by reading the identification information.

60. The system of claim 42, wherein the transporter is configured to perfuse the organ or tissue.

61. Apparatus for holding an organ or a tissue for at least one of perfusion, storage, diagnosis and transport of the organ or tissue, comprising:
an organ or tissue transporter;
a portable housing having one or more heat transfer surfaces;
a compartment within the transporter having one or more heat transfer surfaces arranged on an outer surface of the compartment to transfer heat between a cooling source contained within the compartment and at least a part of one of the one or more heat transfer surfaces of the portable housing, the compartment being liquid-tight and preventing contact between a liquid contained within the compartment and the portable housing; and
an organ or tissue supporting surface configured to support the organ or tissue within said portable housing,
wherein the portable housing is configured to be received by the transporter and wherein at least a portion of at least one of the one or more heat transfer surfaces of the compartment is in contact with at least a portion of at least one of the one or more heat transfer surfaces of the portable housing to allow effective heat transfer to or from the contents of the portable housing,
wherein the portable housing includes openings configured to allow tubing to pass through said openings and be connected to the organ or tissue, and
wherein the tubing can pass through the openings when the portable housing is mated with the compartment.

62. A method of transporting an organ or a tissue, comprising:
placing the organ or tissue in a portable housing, the portable housing having one or more heat transfer surfaces;
placing the portable housing containing the organ or tissue in a compartment of a transporter configured to receive the portable housing, the compartment having one or more heat transfer surfaces arranged on an outer surface of the compartment, the compartment being liquid-tight and preventing contact between a liquid contained within the compartment and the portable housing,
wherein at least a portion of at least one of the one or more heat transfer surfaces of the compartment is in contact with at least a portion of at least one of the one or more heat transfer surfaces of the portable housing;
transferring heat between a cooling source contained within the compartment, via at least a part of one of the one or more heat transfer surfaces of the compartment, to or from the contents of the portable housing; and
transporting the organ in said portable housing in said transporter,
wherein the portable housing includes openings configured to allow tubing to pass through said openings and be connected to the organ, and
wherein the tubing can pass through the openings when the portable housing is mated with the compartment.

* * * * *